(12) United States Patent
Gholap et al.

(10) Patent No.: US 7,756,309 B2
(45) Date of Patent: Jul. 13, 2010

(54) METHOD AND SYSTEM FOR STORING, INDEXING AND SEARCHING MEDICAL IMAGES USING ANATOMICAL STRUCTURES OF INTEREST

(75) Inventors: Abhijeet S. Gholap, Pune (IN); Aparna Joshi, Pune (IN); Chiruvolu V. K. Rao, Pune (IN); Gauri A. Naik, Pune (IN); Prithviraj Jadhav, Pune (IN); Satyakam Sawaimoon, New Mumbai (IN)

(73) Assignee: BioImagene, Inc., Sunnyvale, CA (US)

( * ) Notice: Subject to any disclaimer, the term of this patent is extended or adjusted under 35 U.S.C. 154(b) by 963 days.

(21) Appl. No.: 11/493,857

(22) Filed: Jul. 26, 2006

(65) Prior Publication Data
US 2007/0025606 A1 Feb. 1, 2007

Related U.S. Application Data

(60) Provisional application No. 60/702,953, filed on Jul. 27, 2005.

(51) Int. Cl.
G06K 9/00 (2006.01)
(52) U.S. Cl. .................................................. 382/128
(58) Field of Classification Search .................. 382/128, 382/131, 133, 181, 224
See application file for complete search history.

(56) References Cited

U.S. PATENT DOCUMENTS

| | | | |
|---|---|---|---|
| 5,915,250 A | 6/1999 | Jain et al. | |
| 6,146,897 A * | 11/2000 | Cohenford et al. | 436/63 |
| 6,675,166 B2 | 1/2004 | Bova | |
| 6,678,703 B2 | 1/2004 | Rothschild et al. | |
| 6,785,410 B2 | 8/2004 | Vining et al. | |
| 6,902,935 B2 * | 6/2005 | Kaufman et al. | 436/63 |
| 6,947,586 B2 * | 9/2005 | Kasdan et al. | 382/133 |
| 2003/0176929 A1 | 9/2003 | Gardner | |
| 2004/0082845 A1 * | 4/2004 | Matsumoto et al. | 600/407 |
| 2005/0033736 A1 | 2/2005 | Carlin et al. | |
| 2005/0038776 A1 | 2/2005 | Cyrus et al. | |
| 2005/0096530 A1 * | 5/2005 | Daw et al. | 600/408 |

OTHER PUBLICATIONS

Konig, K. Multiphoton microscopy in life sciences. J. Microsc. 2000; 200(2): 83-104.
McLeod, et al. Pharmacogenomics: Unlocking the human genome for better drug therapy. Annual Review of Pharmacology and Toxicology. 2001; 41: 101-21.
Southern, E., DNA microarrays. History and overview. Methods Mol. Biol. 2001; 170: 1-15.

* cited by examiner

*Primary Examiner*—Tom Y Lu
(74) *Attorney, Agent, or Firm*—Wilson Sonsini Goodrich & Rosati

(57) ABSTRACT

An automated method and system for method and system for indexing, storing and searching medical images using indexed anatomical structures of interest. The method and system provides automated screening of medical images using anatomical structures of interest using a pre-determined hierarchical indexing and searching scheme.

23 Claims, 15 Drawing Sheets

FIG. 9
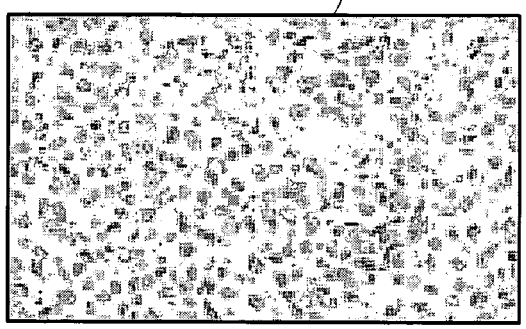
A
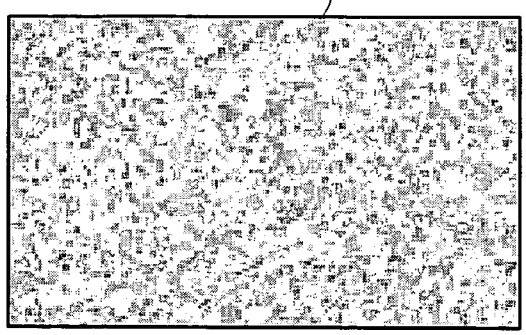
B
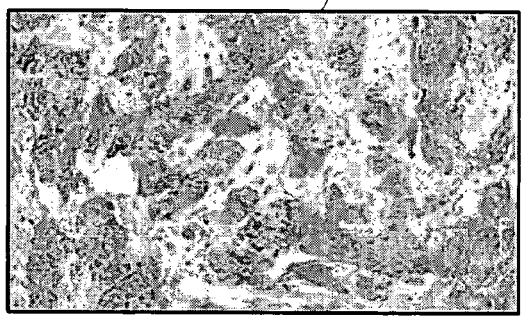
C
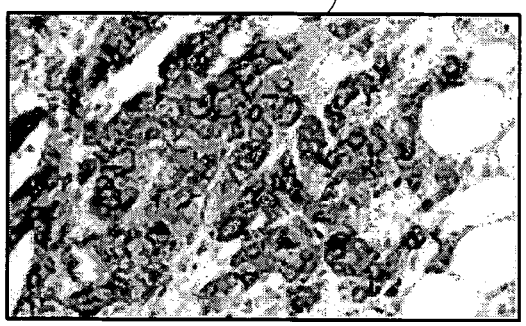
D

FIG. 10
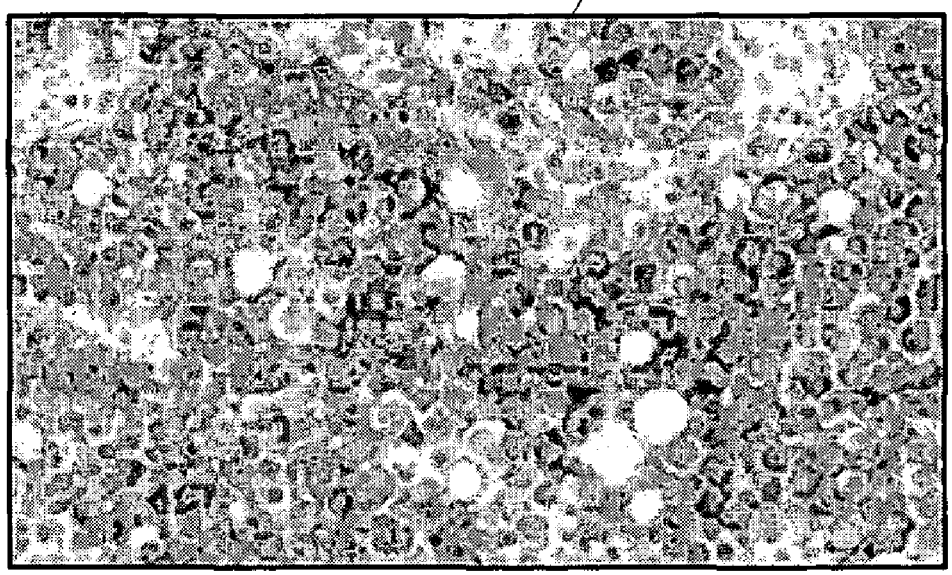
A
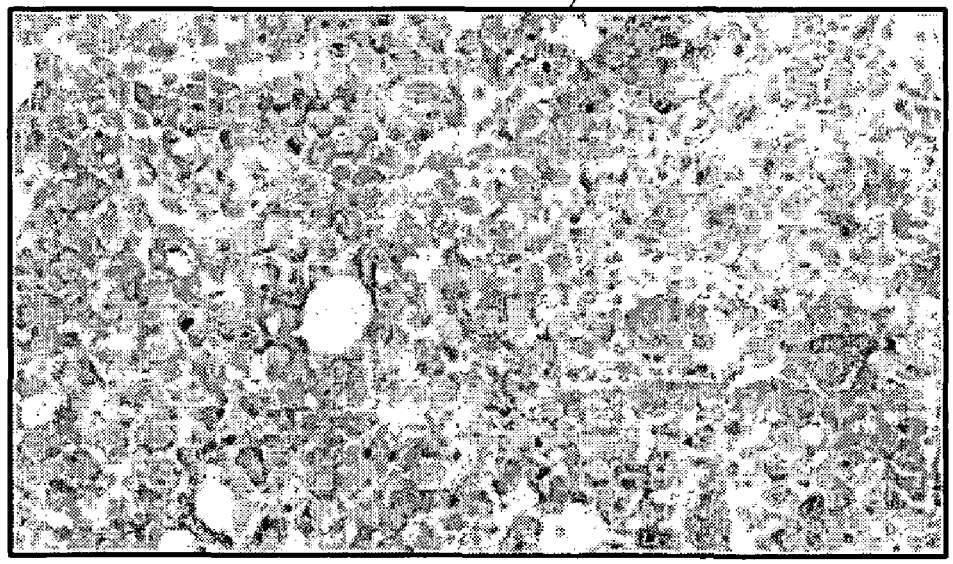
B

IMAGE GROUP ID COMPOSITION

| MEMBRANE SCORE MS | CYTOPLASM SCORE MS | % POSITIVITY PP | CYTOPLASM POSITIVITY CP |
|---|---|---|---|

NUMBER OF DIGITS

| 1 | 1 | 1 | 1 |
|---|---|---|---|

RANGE

| 0-3 | 0-3 | 0-3 | 0-3 |
|---|---|---|---|

METHOD AND SYSTEM FOR STORING, INDEXING AND SEARCHING MEDICAL IMAGES USING ANATOMICAL STRUCTURES OF INTEREST

CROSS REFERENCES TO RELATED APPLICATIONS

This application claims priority to U.S. Provisional Patent Application 60/702,953, filed Jul. 27, 2005, the contents of which are incorporated by reference. This application also claims priority to U.S. patent application Ser. No. 11/361,774, filed Feb. 23, 2006, which claims priority to U.S. Provisional Patent Application No. 60/655,465, filed Feb. 23, 2005, the contents of all of which are incorporated by reference.

COPYRIGHT NOTICE

Pursuant to 37 C.F.R. 1.71(e), applicants note that a portion of this disclosure contains material that is subject to and for which is claimed copyright protection, such as, but not limited to, digital photographs, screen shots, user interfaces, or any other aspects of this submission for which copyright protection is or may be available in any jurisdiction. The copyright owner has no objection to the facsimile reproduction by anyone of the patent document or patent disclosure, as it appears in the U.S. Patent Office patent file or records. All other rights are reserved, and all other reproduction, distribution, creation of derivative works based on the contents of the application or any part thereof are prohibited by applicable copyright law.

FIELD OF THE INVENTION

This invention relates to digital image processing. More specifically, it relates to a method and system for method and system for storing, indexing and searching medical images using anatomical structures of interest.

BACKGROUND OF THE INVENTION

The life sciences research is undergoing a paradigm shift from a traditional laboratory (i.e., wet science) driven approach to a truly information-driven approach. A new understanding of the workings of life at the genetic and molecular levels, together with laboratory automation, likely will make the processes associated with finding new drugs, therapies, and agricultural products faster, cheaper, and more effective. As a result, a formidable volume of data is being generated by innovative technologies such as genomics, combinatorial chemistry, and high-throughput screening at an unprecedented rate.

The challenges that accompany the management of massive volumes of data may be compounded by the fact that life sciences data are often dispersed throughout the research and development (R&D) enterprise, across the public domain, and within the labs of external research partners. The data, which tends to be highly complex and constantly changing, may often be stored in multiple heterogeneous formats such as 3-D chemical structure databases, relational database tables, flat files, text stores, image repositories, web sources and other formats. This data may further reside on different hardware platforms, under different operating systems, and in different database management systems.

Life science and biotechnology experiments use large amount of information and images. Processing and communicating efficiently large amounts of information and images led to the new scientific discipline of image informatics. Life science and biotechnology experiments can be categorized as either diagnostic medical imaging or biotechnology experiment. Biotechnology applications include study in disciplines such as genomics, proteomics, pharmacogenomics and molecular imaging. Diagnostic medical imaging includes Histopathology, Cell-cycle analysis, Genetics, Magnetic resonance imaging (MRI), Digital X-ray and Computed tomography (CT). Converting large amounts of images and raw data generated in these experiments into meaningful information remains a challenge that hinders many investigators.

Genomics: Gene expression microarrays are revolutionizing the biomedical sciences. A DNA microarray consists of an orderly arrangement of DNA fragments representing the genes of an organism. Each DNA fragment representing a gene is assigned a specific location on the array, usually a glass slide, and then microscopically spotted (<1 mm) to that location. Through the use of highly accurate robotic spotters, over 30,000 spots can be placed on one slide, allowing molecular biologists to analyze virtually every gene present in a genome. A cDNA array is a different technology using the same principle; the probes in this case are larger pieces of DNA that are complementary to the genes one is interested in studying. High-throughput analysis of micro-array data requires efficient frame work and tools for analysis, storage and archiving voluminous image data. For example, assay titled ".DNA Microarrays. History and overview" by Southern EM. Methods Molecular Biology Journal, 170: 1-15, 2001 provides an insight into the evolution of DNA microarrays.

Cancer is an especially pertinent target of micro-array technology due to the well-known fact that this disease causes, and may even be caused by, changes in gene expression. Micro-arrays are used for rapid identification of the genes that are turned on and the genes that are turned off in tumor development, resulting in a much better understanding of the disease. For example, if a gene that is turned on in that particular type of cancer is discovered, it may be targeted use in cancer therapy. Today, therapies that directly target malfunctioning genes are already in use and showing exceptional results. Micro-arrays are also used for studying gene interactions including the patterns of correlated loss and increase of gene expression. Gene interactions are studied during drug design and screening. Large number of gene interactions studied during a drug discovery requires efficient frame work and tools for analysis, storage and archiving voluminous image data.

Proteomics: Proteomics is the study of the function of all expressed proteins and analysis of complete complements of proteins. Proteomics includes the identification and quantification of proteins, the determination of their localization, modifications, interactions, activities, and, ultimately, their function. In the past proteomics is used for two-dimensional (2D) gel electrophoresis for protein separation and identification. Proteomics now refers to any procedure that characterizes large sets of proteins. Rapid growth of this field is driven by several factors—genomics and its revelation of more and more new proteins; powerful protein technologies, such as newly developed mass spectrometry approaches, global [yeast] two-hybrid techniques, and spin-offs from DNA arrays. For example, Tyers M, Mann M. provides a vivid picture in article titled ". From genomics to proteomics" in Nature Journal 2003, 13; 422(6928): 193-7. Large-scale data sets for protein-protein interactions, organelle composition, protein activity patterns and protein profiles in cancer patients are generated in the past few years. Rapid analysis of these data sets requires innovative information driven framework and tools to process, analyze, and interpret prodigious amounts of data.

Tissuemicroarray (TMA) works on the similar principles of DNA microarray where large number of tissue samples are placed on a single slide and analysed for these expression of proteins. The image data generated in such cases is tremendous and require efficient software analysis tools. TMA may involve reporting protein to be detected by IHC, immunofluorescence, luminescence, absorbance, and reflection detection.

Pharmacogenomics: There is great heterogeneity in the way humans respond to medications, often requiring empirical strategies to find the appropriate drug therapy for each patient. There has been great progress in understanding the molecular basis of drug action and in elucidating genetic determinants of disease pathogenesis and drug response. Pharmacogenomics is the field of investigation that aims to elucidate the inherited nature of inter-individual differences in drug disposition and effects, with the ultimate goal of providing a stronger scientific basis for selecting the optimal drug therapy and dosages for each patient. These genetic insights should also lead to mechanism-based approaches to the discovery and development of new medications. For example, assay by Howard L McLeod, William E Evans titled "PHARMACOGENOMICS: Unlocking the Human Genome for Better Drug Therapy" in Annual Review of Pharmacology and Toxicology 2001, Vol. 41: 101-121 describes the scope of pharmacogenomics. Collection, analysis and maintenance of inter-individual differences data sets requires efficient information driven framework and tools to process, analyze, and interpret prodigious amounts of data.

Microscopy: Molecular imaging—Identification of changes in the cellular structures indicative of disease remains the key to the better understanding in medicinal science. Microscopy applications as applicable to microbiology (e.g., gram staining, etc.), Plant tissue culture, animal cell culture (e.g. phase contrast microscopy, etc.), molecular biology, immunology (e.g., ELISA, etc.), cell biology (e.g., immunofluorescence, chromosome analysis, etc.) Confocal microscopy: Time-Lapse and Live Cell Imaging, Series and Three-Dimensional Imaging. The advancers in confocal microscopy have unraveled many of the secrets occurring within the cell and the transcriptional and translational level changes can be detected using fluorescence markers. The advantage of the confocal approach results from the capability to image individual optical sections at high resolution in sequence through the specimen. Framework with tools for 3-Dimensional analysis of thicker sections, differential color detection, FISH etc is needed to expedite the progress in this area.

Near infrared (NIR) multiphoton microscopy—is becoming a novel optical tool for fluorescence imaging with high spatial and temporal resolution, diagnostics, photochemistry and nanoprocessingu within living cells and tissues. NIR lasers can be employed as the excitation source for multifluorophor multiphoton excitation and hence multicolour imaging. In combination with fluorescence in situ hybridization (FISH), this novel approach can be used for multi-gene detection (multiphoton multicolour FISH). For example, assay titled "Multiphoton microscopy in life sciences" by Konig K. in Journal of Microscopy, 2000, Vol. 200 (Part 2):83-104 indicates the state of microscopy in life sciences.

In-vivo imaging: Animal models of cancer are inevitable in studies that are difficult or impossible to perform in people. Imaging of in-vivo markers permit observations of the biological processes underlying cancer growth and development. Functional imaging—the visualization of physiological, cellular, or molecular processes in living tissue—would allows to study metabolic events in real time, as they take place in living cells of the body.

Diagnostic medical imaging: Imaging technology has broadened the range of medical options in exploring untapped potential for cancer diagnosis. X-ray mammography already has had a lifesaving effect in detecting some early cancers. Computed tomography (CT) and ultrasound permit physicians to guide long, thin needles deep within the body to biopsy organs, often eliminating the need for an open surgical procedure. CT scan images can reveal whether a tumor has invaded vital tissue, grown around blood vessels, or spread to distant organs; important information that can help guide treatment choices. Three dimensional image reconstruction and visualization techniques require significant processing capabilities using smaller, faster, and more economical computing solutions.

The conventional process for managing medical images is completed at most hospitals, clinics and imaging centers. The medical image is printed onto sheets of film, which are delivered to the radiologist for interpretation. After the transcribed report is delivered to the radiologist, reviewed for errors and signed, the films and report are delivered or mailed to the referring doctor. This process often takes several days, up to a week. If questions arise, the referring doctor contacts the radiologist, who may be forced to rely upon memory, having reviewed the films several days before and no longer has possession of them. Also, the referring doctor must then manage the hard-copy films, either by filing the films in his office, or returning the films to the imaging center or hospital to be filed, depending upon practices in the local community. If the patient then goes to a second doctor, requires surgery, or requires another medical imaging procedure, the films must be located and physically carried or shipped to the hospital, surgery center, or to the second doctor's office. There are numerous opportunities for films to be lost or misfiled, and doctors who maintain more than, one office may not always have the correct patient films in the correct office.

The current film-based system is very expensive, and the charges for films, processing chemicals, and delivery can easily add up to $30 to $50 per MRI patient study. Other problems for the imaging facility are the numerous opportunities for the films to be physically lost, as well as the considerable time, personnel, and expense required for the delivery and retrieval of these films. Estimates are that up to 25% of medical images are not accessible when required.

Several researchers have performed experiments on and made observations of biological tissue samples suggesting that a molecular basis for cancer and other diseases might be discovered through careful molecular analysis of such tissues. Such an understanding could permit improvement in the diagnosis, screening, and treatment of disease, and could permit disease treatment to be tailored to the specific molecular defects found in an individual patient. Many different researchers and laboratories study the molecular basis of disease and a large amount of data and information is produced from such studies. Optimization of the handling and integration research results, data, and other information produced and used by various laboratories devoted to studying the molecular basis of cancer and other tissue-based diseases is advantageous for realizing improvements in the understanding and treatment of disease.

Even though many large genomic warehouse databases currently exist, and even though scientific laboratories are connected to the Internet, the data produced by a lab are not necessarily well handled, integrated, validated, searchable, and useable either by the lab producing the data or by another lab that might be interested in using the data. Generally, when data from biological tissue studies are published, only a limited set of the actual primary data (and sometimes none of it) are available for review and reanalysis. Moreover, common language and reference points are often not used for reporting the data. Even in the lab that did the original work, there is often no efficient or robust way to integrate data from a study with previous or subsequent studies. Furthermore, because of space limitations and the difficulty of tracking complex research methods, many published descriptions of laboratory methods do not provide adequate information for another scientist to accurately reproduce an experiment, even though this is a central tenet of scientific publication. The end result is that when taken as a group, the many similar or related studies, while individually illuminating, are isolated and autonomous from each other, and do not achieve potential synergies.

Lack of proper data handling may result in major problems that may slow or possibly prevent real progress in finding better treatment and diagnostic methods for major diseases. In particular, current methods of disseminating information from molecular studies of cancer and other diseases do not allow results from one study to be easily integrated with results from other studies. There is no standard way to link the results of DNA, RNA, and protein-based studies to cellular function or phenotype expression. Current methods of dissemination of the results of molecular studies do not allow preservation of a substantial portion of the original data supporting such studies, making it difficult for researchers to verify the conclusion of a research study or otherwise reinterpret the data.

The ability to detect, through imaging, the histopathological image data for the molecular and phenotypic changes associated with a tumor cell will enhance pathologists ability to detect and stage tumors, select appropriate treatments, monitor the effectiveness of a treatment, and determine prognosis.

A standard test used to measure protein expression is immunohistochemistry (IHC). Analyzing the tissue samples stained with imnunohistochemical (IHC) reagents has been the key development in the practice of pathology. Normal and diseased cells have certain physical characteristics that can be used to differentiate them from each other. These characteristics include complex patterns, rare events, and subtle variations in color and intensity Hematoxillin and Eosin (H&E) method of staining is used to study the morphology of tissue samples. Based on the differences and variations in the patterns from the normal tissue, the type of cancer is determined. Also the pathological grading or staging of cancer (Richardson and Bloom Method) is determined using the H&E staining. This pathological grading of cancer is not only important from diagnosis angle but has prognosis value attached to it.

One of the main limitations of the prior art is the scope of the term "image content." Content is often represented by image parameters and has little or no relevance to the objective of the study being carried out. A consequence of this interpretation of content is the images retrieved may look similar from image dimensions, but may not be having similar pathological/radiological properties. For example, two images of the different tissues with malignancies might look different to a normal eye. It is pathologist's knowledge and experience that differentiates the types of malignancies. However, pathologists grade both these images as similar and assign membrane score (e.g., 3+).

There have been many attempts to solve some of the problems associated with automated analysis of medical images. For example, in U.S. Pat. No. 6,675,166, entitled "Integrated multidimensional database" that issued to Bova teaches "a method of distributing research data from a common database to a user of the common database is provided. Data concerning research results and data upon which the research results are based are stored in a local database and are linked to each other. Data concerning research results and data upon which the research results are based are selectively extracted from the local database to the common database. Research data are then selected by a user of the common database from the extracted data concerning research results and from the data upon which the extracted data are based and the selected research data are distributed to the user."

U.S. Pat. No. 6,678,703, entitled "Medical image management system and method" that issued to Rothschild et al. teaches "a medical image management system and method that uses a central data management system to centrally manage the storage and transmission of electronic records containing medical images between remotely located facilities. A polling system is provided with remotely located workstations or local workstations so that the remote or local workstations may request queued data to be delivered that is awaiting delivery in the central database management system. The remotely located workstation or local image workstation communicates with a remotely located central data management system via a remote interface over the internet. The central database management system maintains and update any changes in the IP address of a remote or local workstation, in a look up table. The central data management system may also, in addition, push data when received to the last known IP address in the look up table.

U.S. Pat. No. 6,785,410, entitled "Image reporting method and system" that issued to Vining, et al., teaches "a method and system are provided to report the findings of an expert"s analysis of image data. The method and system are based on a reporting system that forms the basis of an image management system that can efficiently and systematically generate image reports, facilitate data entry into searchable databases for data mining, and expedite billing and collections for the expert's services. The expert identifies a significant finding on an image and attaches a location:description code to the location of that finding in order to create a significant finding and an entry into a database. Further descriptions of that finding, such as dimensional measurements, may be automatically appended to the finding as secondary attributes. After the evaluation, the system sorts the findings in the database and presents the findings by prioritized categories. The expert edits and approves a multimedia report which may be delivered by electronic means to an end-user."

In U.S. Pat. No. 5,915,250, entitled "Threshold-based comparison," that issued to Jain teaches "a system and method for content-based search and retrieval of visual objects. A base visual information retrieval (VIR) engine utilizes a set of universal primitives to operate on the visual objects. An extensible VIR engine allows custom, modular primitives to be defined and registered. A custom primitive addresses domain specific problems and can utilize any image understanding technique. Object attributes can be extracted over the entire image or over only a portion of the object. A schema is defined as a specific collection of primitives. A specific schema implies a specific set of visual features to be processed and a corresponding feature vector to be used for content-based similarity scoring. A primitive registration interface registers custom primitives and facilitates storing of an analysis function and a comparison function to a schema table. A heterogeneous comparison allows objects analyzed by different schemas to be compared if at least one primitive is in common between the schemas. A threshold-based comparison is utilized to improve performance of the VIR engine. A distance between two feature vectors is computed in any of the comparison processes so as to generate a similarity score.

In U.S. Published Patent Application, 20030176929, entitled "User interface for a bioinformatics system," published by Gardner, teaches "a bioinformatics system and method is provided for integrated processing of biological data. According to one embodiment, the invention provides an interlocking series of target identification, target validation, lead identification, and lead optimization modules in a discovery platform oriented around specific components of the drug discovery process. The discovery platform of the invention utilizes genomic, proteomic, and other biological data stored in structured as well as unstructured databases. According to another embodiment, the invention provides overall platform/architecture with integration approach for searching and processing the data stored in the structured as well as unstructured databases. According to another embodiment, the invention provides a user interface, affording users the ability to access and process tasks for the drug discovery process."

In U.S. Published Patent Application, 20050033736, entitled "System and method for processing record related information, published by Carlin, teaches "A system and method is disclosed for defining a set of predetermined comment codes for incorporation into database records to enhance processes and workflows. The system comprises a repository of records, including a plurality of records incorporating at least one comment identifier identifying a comment associated by a user with a particular record and provides additional information about a particular characteristic of the record, a search processor for searching the repository to identify a plurality of records incorporating at least one predetermined comment identifier in response to a user provided search query, and a task processor for assigning performance of a task comprising processing the identified plurality of records. The system may also include a report generator for generating a report identifying the plurality of records incorporating the predetermined comment identifier and for providing data representing the report in a format suitable for at least one of, display on a reproduction device, printing and electronic communication, in response to a user command."

In U.S. Published Patent Application, 20050038776, entitled, "Information system for biological and life sciences research," published by Cyrus teaches "an online life science research environment and virtual community with a focus on design and analysis of biological experiments includes a life sciences laboratory system employing at least one networked computer system that defines a virtual research environment. Users access the system through a portal associated with the networked computer system(s). The virtual research environment has a data coupling mechanism by which the user designates a set of user-specified data for bioinformatics processing. A processor(s) associated with the networked computer system(s) performs bioinformatics services upon the user-specified data. In one embodiment, the data coupling mechanism enables transfer of the user-specified data to a memory space that is mediated or accessed by the processor performing the bioinformatics processing. Users may thus exploit bioinformatics processing resources that are not deployed on users' local computer environments, and to store and organize information relating to life sciences research in a secure, online workspace."

Picture Archiving and Communication Systems (PACS): Several solutions have been developed with the intention of streamlining the storage and accessibility of medical images by managing, electronic records that include the images in electronic form that may be converted for viewing, such as on screen displays or via film printers. "Picture Archiving and Communications Systems" (PACS) generally provides medical image management via a collection of components that enable image data acquisition, transmission, display, and, storage. Such systems are implemented in imaging clinics and hospitals to make the digital data available at different locations within the radiology department or the facility. Further, the use of such systems is generally restricted to in-house radiology and other departments, thus excluding the referring physicians, who are outside the imaging facility. These systems have high price tags for the local installation of the respective central image management and storage systems generally required, and involve other high costs related to additional personnel to configure and maintain such image management systems locally onsite at the imaging facility.

Medical Images and Internet Application Service Providers (ASP): Medical image management market is large, and represents large volumes of recurring transmissions of electronic records associated with medical images. Several efforts have recently been made to replace or at least significantly enhance the conventional film-based systems and methods for medical image management by managing these images electronically, and more particularly via an internet-based ASP model. However, the concept of an Internet based Application Service Provider (ASP) for the transmission and storage of medical images is an industry in embryonic stage. Very few of the diagnostic imaging procedures performed annually in the U.S. are being transmitted and/or stored utilizing an ASP model.

There are several vendors supplying PACS. Amicas, www.amicas.com has supplied its vision series to several leading hospitals in US. eMed Technologies is a Healthcare Application Service Provider (HASP), www.emed.com, provides eMed.net service including a medical image viewing application with integrated access to medical images and reports along with other relevant information through a physician's web site. General Electric Medical systems, www.ge-.com, has a product Centricity™ PACS. Centricity™ PACS is at the heart of GE's integrated approach to improving radiology workflow. By itself, Centricity™ PACS includes image communication within a radiology department. When integrated with Centricity™ RIS, it creates a single workflow engine—Centricity™ RIS/PACS—that allows radiologists to access comprehensive patient information at a single workstation via a single login anywhere in the enterprise.

Image Medical, www.eradimagemedical.com has a product "eRAD". It is a PACS and Teleradiology System that web-enabled access to patient studies and reports from a standard PC with Internet access at a moment's notice. Radiologists, Referring Physicians, System Administrators and other authorized users may easily log on from anywhere to access diagnostic-quality, pre-fetched images from dynamic IP addresses. The patient studies may be received uncompressed or compressed, as selected by the user.

Over the last one decade, there has been tremendous progress in the theory and design of "search engine optimization." Google is leading in several aspects of the search engine research, and Google's data structures are optimized so that a large document collection can be crawled, indexed, and searched with little cost. See "The Anatomy of a Large-Scale Hypertextual Web Search Engine" by Sergey Brin and Lawrence Page. Although, CPUs and bulk input output rates have improved dramatically over the years, a disk seek still requires about 10 ms to complete. Google is designed to avoid disk seeks whenever possible, and this has had a considerable influence on the design of search data structures.

However, none of these solutions solve all of the problems associated with automatically analyzing anatomical structures of interest. Thus, it is desirable to provide a method and system automated digital image analysis using anatomical structures of interest.

SUMMARY OF THE INVENTION

In accordance with preferred embodiments of the present invention, some of the problems associated with automated biological sample analysis systems are overcome. A method and system method and system for storing, indexing and searching medical images using anatomical structures of interest.

The method and system provides an automated method and system for indexing, storing and searching medical images using indexed anatomical structures of interest. The method and system provides automated screening of medical images using anatomical structures of interest via hierarchical indexing and searching.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 9 are block diagrams of digital photographs which belong to three different image groups based on membrane (Her2neu) scores;

FIG. 10 are block diagrams of digital photographs illustrating a grouping of images;

FIG. 11 is a block diagram illustrating an exemplary method for image group ID composition;

DETAILED DESCRIPTION OF THE INVENTION

Exemplary Biological Sample Analysis System

Figure 1:
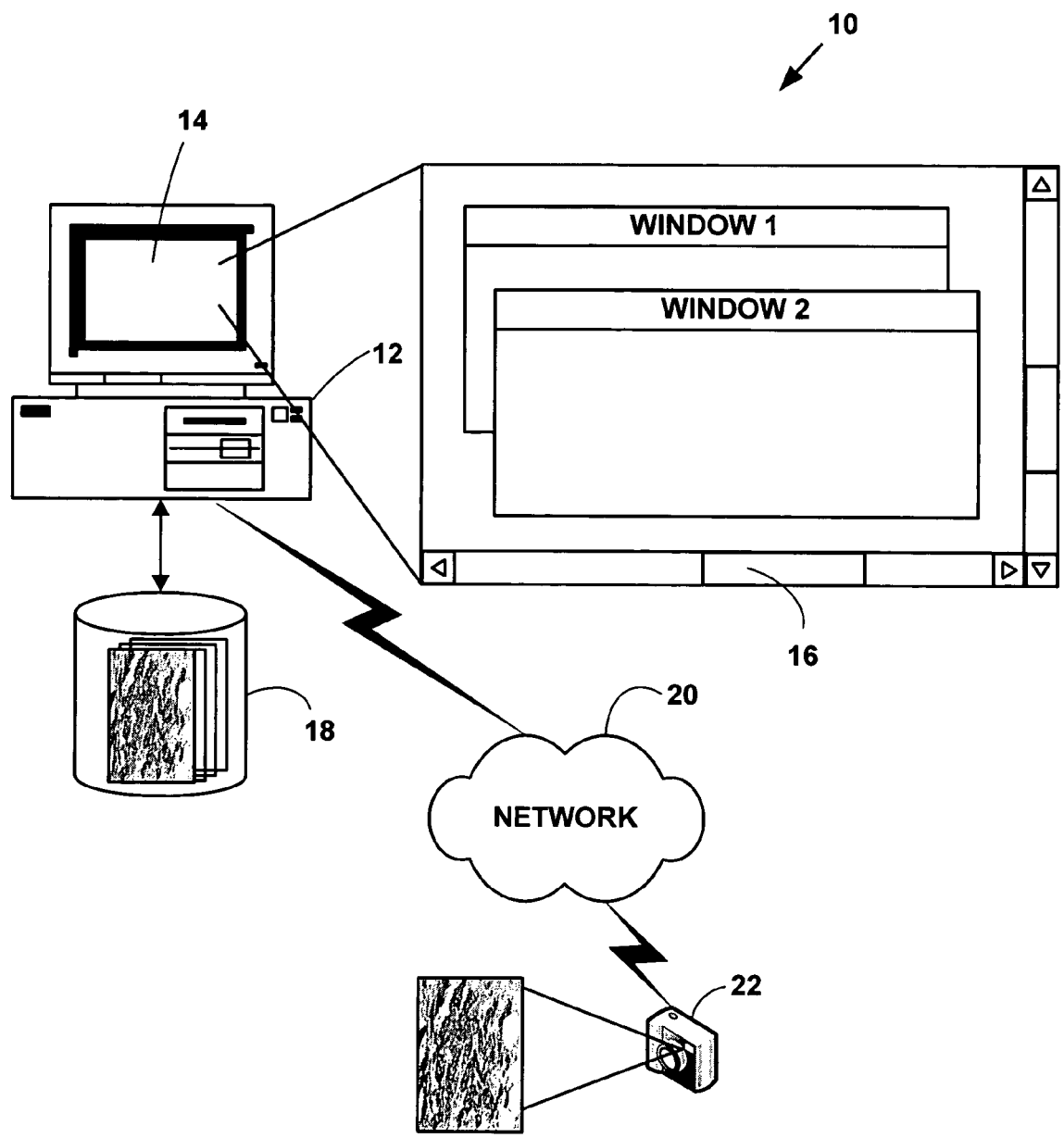
FIG. 1 is a block diagram illustrating an exemplary automated biological sample analysis system.

FIG. 1 is a block diagram illustrating an exemplary biological sample analysis system 10. The exemplary biological sample analysis system 10 includes one or more computers 12 with a computer display 14 (one of which is illustrated). The computer display 14 presents a windowed graphical user interface ("GUI") 16 with multiple windows to a user. The present invention may optionally include a microscope or other magnifying device (not illustrated in FIG. 1). One or more databases 18 (one or which is illustrated) include biological sample information in various digital images or digital data formats. The databases 18 may be integral to a memory system on the computer 12 or in secondary storage such as a hard disk, floppy disk, optical disk, or other non-volatile mass storage devices. The computer 12 and the databases 18 may also be connected to an accessible via one or more communications networks 20. The system 10 also includes a digital camera 22 and/or analog camera.

The one or more computers 12 may be replaced with client terminals in communications with one or more servers, or with personal digital/data assistants (PDA), laptop computers, mobile computers, Internet appliances, one or two-way pagers, mobile phones, or other similar desktop, mobile or hand-held electronic devices.

The communications network 20 includes, but is not limited to, the Internet, an intranet, a wired Local Area Network (LAN), a wireless LAN (WiLAN), a Wide Area Network (WAN), a Metropolitan Area Network (MAN), Public Switched Telephone Network (PSTN) and other types of communications networks 22.

The communications network 20 may include one or more gateways, routers, or bridges. As is known in the art, a gateway connects computer networks using different network protocols and/or operating at different transmission capacities. A router receives transmitted messages and forwards them to their correct destinations over the most efficient available route. A bridge is a device that connects networks using the same communications protocols so that information can be passed from one network device to another.

The communications network 20 may include one or more servers and one or more web-sites accessible by users to send and receive information useable by the one or more computers 12. The one ore more servers, may also include one or more associated databases 18 for storing electronic information.

The communications network 20 includes, but is not limited to, data networks using the Transmission Control Protocol (TCP), User Datagram Protocol (UDP), Internet Protocol (IP) and other data protocols.

As is know in the art, TCP provides a connection-oriented, end-to-end reliable protocol designed to fit into a layered hierarchy of protocols which support multi-network applications. TCP provides for reliable inter-process communication between pairs of processes in network devices attached to distinct but interconnected networks. For more information on TCP see Internet Engineering Task Force (ITEF) Request For Comments (RFC)-793, the contents of which are incorporated herein by reference.

As is know in the art, UDP provides a connectionless mode of communications with datagrams in an interconnected set of computer networks. UDP provides a transaction oriented datagram protocol, where delivery and duplicate packet protection are not guaranteed. For more information on UDP see IETF RFC-768, the contents of which incorporated herein by reference.

As is known in the art, IP is an addressing protocol designed to route traffic within a network or between networks. IP is described in IETF Request For Comments (RFC)-791, the contents of which are incorporated herein by reference. However, more fewer or other protocols can also be used on the communications network 20 and the present invention is not limited to TCP/UDP/IP.

The one or more databases 18 include plural digital images of biological samples taken with a camera such as a digital camera and stored in a variety of digital image formats including, bit-mapped, joint pictures expert group (JPEG), graphics interchange format (GIF), etc. However, the present invention is not limited to these digital image formats and other digital image or digital data formats can also be used to practice the invention.

The digital images are typically obtained by magnifying the biological samples with a microscope or other magnifying device and capturing a digital image of the magnified biological sample (e.g., groupings of plural magnified cells, etc.) with a camera (e.g., digital camera 22).

The term "sample" includes, but is not limited to, cellular material derived from a biological organism. Such samples include but are not limited to hair, skin samples, tissue samples, cultured cells, cultured cell media, and biological fluids. The term "tissue" refers to a mass of connected cells (e.g., central nervous system (CNS) tissue, neural tissue, or eye tissue) derived from a human or other animal and includes the connecting material and the liquid material in association with the cells. The term "biological fluid" refers to liquid material derived from a human or other animal. Such biological fluids include, but are not limited to, blood, plasma, serum, serum derivatives, bile, phlegm, saliva, sweat, amniotic fluid, and cerebrospinal fluid (CSF), such as lumbar or ventricular CSF. The term "sample" also includes media containing isolated cells. The quantity of sample required to obtain a reaction may be determined by one skilled in the art by standard laboratory techniques. The optimal quantity of sample may be determined by serial dilution.

An operating environment for the devices biological sample analysis processing system 10 include a processing system with one or more high speed Central Processing Unit(s) ("CPU"), processors and one or more memories. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU-executed," or "processor-executed."

It will be appreciated that acts and symbolically represented operations or instructions include the manipulation of electrical signals by the CPU or processor. An electrical system represents data bits which cause a resulting transformation or reduction of the electrical signals or biological signals, and the maintenance of data bits at memory locations in a memory system to thereby reconfigure or otherwise alter the CPU's or processor's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM"), flash memory, etc.) mass storage system readable by the CPU. The computer readable medium includes cooperating or interconnected computer readable medium, which exist exclusively on the processing system or can be distributed among multiple interconnected processing systems that may be local or remote to the processing system.

Figure 2:
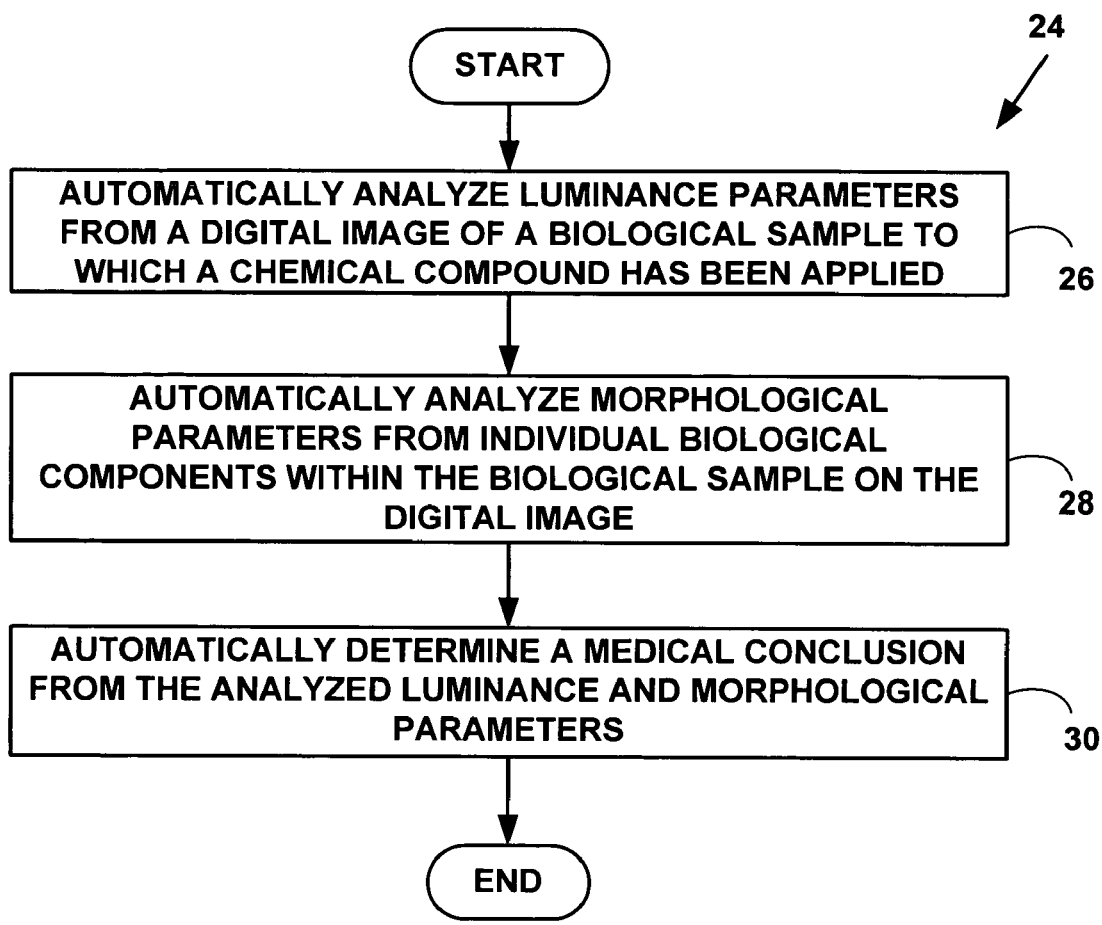
FIG. 2 is a flow diagram illustrating an exemplary method for automated biological sample analysis.

FIG. 2 is a flow diagram illustrating an exemplary Method 24 for automated biological sample analysis. At Step 26, pre-determined parameters from a digital image of a biological sample to which a chemical compound has been applied are modified to make a set of plural biological objects in the digital image more distinct. At Step 28, plural biological objects of interest are located in the set of plural biological objects made more distinct. At Step 30, the located biological objects of interest are identified and classified to determine a medical diagnosis conclusion.

In one embodiment, Method 24 is used for automated analysis of tissues potentially including human prostate and breast cancers.

Report or description of anatomic structures of interest is one key output from a life science study or medical diagnosis. However, there are no reports indicating efforts made to standardize such a report structure. For example in DICOM standards, Structured Report (SR) Document is included. However, this standard does not include a structure for description. One of the consequences of unstructured description is that the text in SR document cannot be used for searching respective image data base efficiently. In the present invention a structure for describing anatomic structures of interest is presented that is used for efficient data base search.

In one embodiment, three dominant areas of anatomic structure of interest analysis for life sciences research or diagnostic purposes are used, namely, radiological pathological and cytological analysis. However, the present invention is not limited to this embodiment and other embodiments can also be used to practice the invention.

Radiological studies include X-ray, Fluoroscopic studies, Barium studies, Ultrasonography, 2D-echocardiography, Colour Doppler studies, CT scan, MRI, PET images. Histopathological studies are carried out on various types of tissues/organs. Cytological studies are carried out to study biological materials including various body fluids as well as solid tissues/organs.

Exemplary Anatomic Structures

Figure 3:
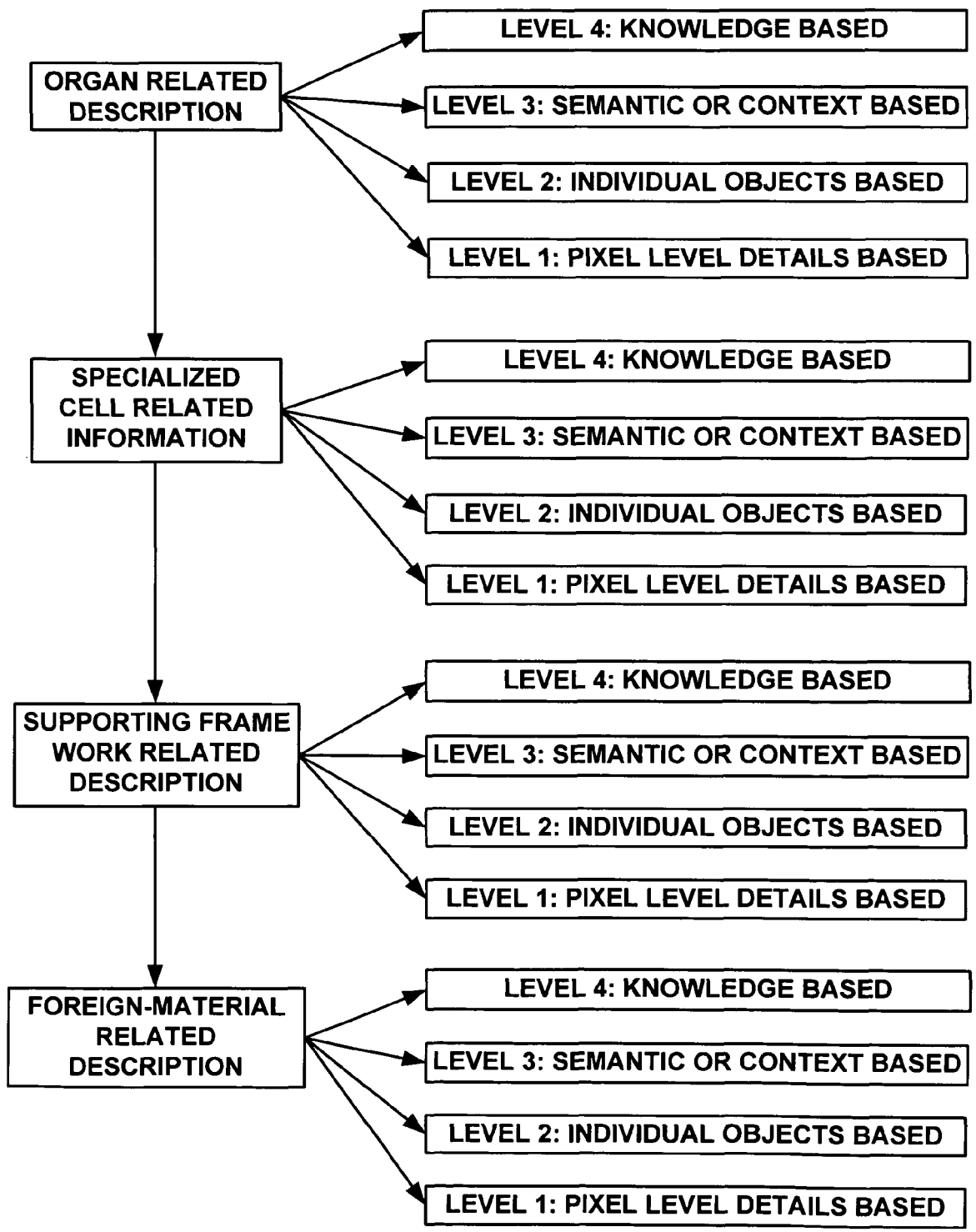
FIG. 3 is a block diagram illustrating exemplary anatomic and description structures.

FIG. 3 is a block diagram 32 illustrating exemplary anatomic and description structures. The exemplary anatomic and description structures are used to index digital images.

In one embodiment, the content description of an anatomic structure of interest is divided into four parts:

1) Organ-related description,
2) Specialized cells-related description,
3) Supporting framework-related description, and
4) Foreign material-related description.

However, the present invention is not limited to this embodiment and more, fewer or other parts can be used for an anatomic structure of interest.

Description in each of these parts has different significance depending on the nature of the information, reliability and accuracy of measuring such information.

Measurements made based on life science knowledge and expertise have highest significance. Next are measurements that are context-dependent. Next are those measurements carried out at individual biological cells or units level.

Indexing Digital Images

Figure 4:
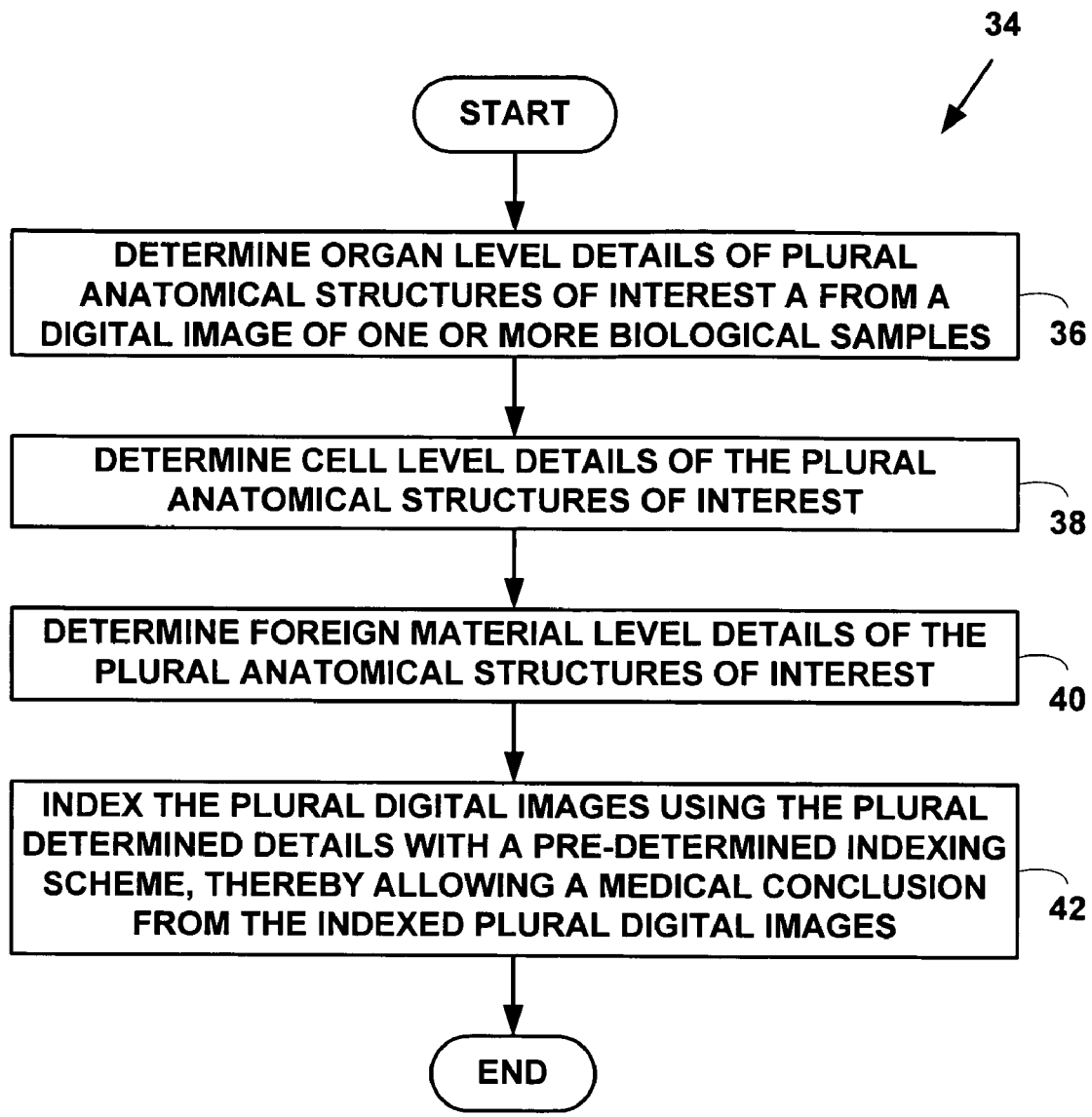
FIG. 4 is a flow diagram illustrating a method for determining anatomical structures of interest.

FIG. 4 is a flow diagram illustrating a Method 34 for indexing plural anatomical structures of interest in plural digital images of a biological sample to which a chemical compound has been applied. At Step 36, organ level details of plural anatomical structures of interest are determined from a digital image. At Step 38, cell level details of the plural anatomical structures of interest are determined. At Step 40, foreign material level details of the plural anatomical structures of interest are determined. At Step 42, the plural digital images are indexed using the plural determined details with a pre-determined indexing scheme, thereby allowing a medical conclusion from the indexed plural digital images.

In one embodiment, Method 34 further includes an additional Step 43 comprising determining framework level details. However, Method 34 can be practiced without Step 43.

Figure 5:
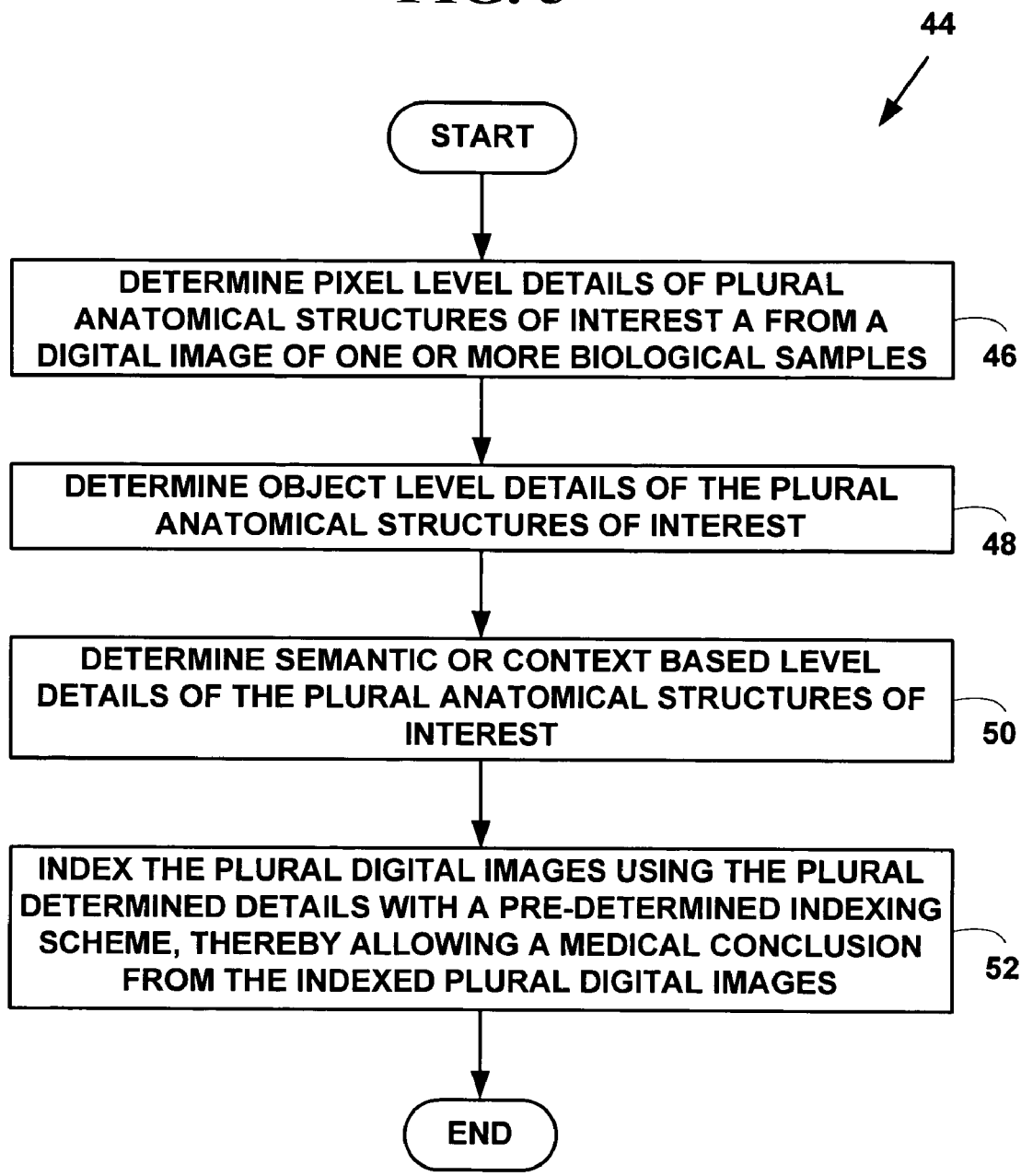
FIG. 5 is a flow diagram illustrating a method for determining anatomical structures of interest.

FIG. 5 is a flow diagram illustrating a Method 44 for indexing plural anatomical structures of interest in plural digital images of a biological sample to which a chemical compound has been applied. At Step 46, pixel level details of plural anatomical structures of interest are determined from a digital image. At Step 48, object level details of the plural anatomical structures of interest are determined. At Step 50, semantic or context based level details of the plural anatomical structures of interest are determined. At Step 52, the plural digital images are indexed using the plural determined details with a pre-determined indexing scheme, thereby allowing a medical conclusion from the indexed plural digital images.

In one embodiment, Method 44 further include an additional Step 53 comprising determining, knowledge based level details of the plural anatomical structures of interest. However, Method 44 can be practiced without Step 53.

Providing information manually is difficult for human pathologists and life science researchers. Embodiments of the invention provide low level information automatically, accurately and consistently.

In one embodiment of Methods 34 and 44 a indexing scheme and related information hierarchy similar to that used for searching and indexing information on the Internet is used to search plural digital images for plural anatomical structures of interest to determine a medical conclusion (e.g., a human cancer diagnosis, etc.). The information hierarchy includes BigFiles, Repositories, Document Indexes, Lexicons and Inverted Index. However, the present invention is not limited to such an exemplary embodiment and other embodiments can also be used to practice the invention. Other alternative embodiments are also described herein for the pre-determined indexing scheme.

BigFiles: BigFiles are virtual files spanning multiple file systems and are addressable by 64 bit integers. The allocation among multiple file systems is handled automatically. The BigFiles package also handles allocation and deallocation of file descriptors, since the operating systems do not provide enough for our needs. BigFiles also support rudimentary compression options.

Repository: The repository contains the full HTML of every web page. Each page is compressed using zlib (see RFC1950). In the repository, the documents are stored one after the other and are prefixed by docID, length, and URL. The repository requires no other data structures to be used in order to access it. This helps with data consistency and makes development much easier; other data structures are rebuilt from only the repository and a file which lists crawler errors.

Document Index: The document index keeps information about each document. It is a fixed width ISAM (Index Sequential Access Mode) index, ordered by docID. The information stored in each entry includes the current document status, a pointer into the repository, a document checksum, and various statistics. If the document has been crawled, it also contains a pointer into a variable width file called docinfo which contains its URL and title. Otherwise the pointer points into the URLlist which contains just the URL.

Lexicon: The lexicon has several different forms. One ichange from earlier systems is that the lexicon can fit in memory for a reasonable price. In the current implementation we can keep the lexicon in memory on a machine with 256 MB of main memory. The current lexicon contains 14 million words (though some rare words were not added to the lexicon).

Inverted Index: The inverted index consists of the same barrels as the forward index, except that they have been processed by the sorter. For every valid wordID, the lexicon contains a pointer into the barrel that wordID falls into. It points to a doclist of docID's together with their corresponding hit lists. This doclist represents all the occurrences of that word in all documents.

One option is to sort a doclist is sorted by docID. This allows for quick merging of different doclists for multiple word queries. Another option is to store them sorted by a ranking of the occurrence of the word in each document. This makes answering one word queries trivial and makes it likely that the answers to multiple word queries are near the start. However, merging is much more difficult. Also, this makes development much more difficult in that a change to the ranking function requires a rebuild of the index.

In one embodiment a compromise between these options, keeping two sets of inverted barrels—one set for hit lists which include title or anchor hits and another set for all hit lists. This way, we check the first set of barrels first and if there are not enough matches within those barrels we check the larger ones.

In a white paper Oracle described Oracle interMedia. Oracle interMedia uses object data types, similar to Java or C++ classes, to describe image, audio, and video data. These object data types are called ORDImage, ORDAudio, and ORDVideo, respectively. An instance of these object data types consists of attributes, including metadata and the multimedia content, and methods. Multimedia content is the actual image, audio, or video data. Metadata is format information about the multimedia content, including information such as object length, compression or format, or application provided information (for example, a singer's name for a digital audio song). Methods are procedures that can be performed on the object such as store, deliver, or extract metadata, and compress or convert image format.

In one specific exemplary embodiment, the Oracle object data types are used to practice the invention. However, the present invention is not limited to such an embodiment and other embodiments can also be used to practice the invention.

IHC of histopathology is used to illustrate the concept of descriptors. Table 1 illustrates a list of parameters and their respective significance level. The nature of each of the parameters, number of possibilities for each parameter and weight given to each parameter are indicated. Nature indicates whether the parameter value is in a range "R" like percentage 10-25, or fixed "F" like 0+,1+,2+,3+. Number of possibilities indicates the variations in parameter values. For example, percentage positivity can be from zero to 100, or 101 possibilities. "M" score is 4 possibilities, 0+, 1+, 2+ and 3+. Weight given to each parameter is dependent on the level to which the parameter belongs and the total number of parameters in that level as well as those above. Level 4 will have highest significance and level 1 will have lowest significance. Weights are calculated starting from level 4, using an equation. Table 1 summarizes an exemplary weighting scheme that can be used with the method and system described herein.

TABLE 1

| Sl. no | Name | Level | Nature | Possibilities | Weight |
|---|---|---|---|---|---|
| 1 | % N positivity | 4 | R | 100(10)$ | 1/5 |
| 2 | M score | 4 | F | 4 | 1/5 |
| 3 | C % positivity | 4 | R | 100(10) | 1/5 |
| 4 | C score | 4 | F | 4 | 1/5 |
| 5 | NC percentage | 3 | F | 4 | 1/25 |
| 6 | NM percentage | 3 | F | 4 | 1/25 |
| 7 | CM percentage | 3 | F | 4 | 1/25 |
| 8 | NCM percentage | 3 | F | 4 | 1/25 |
| 9 | % cells with C, 1+ | 2 | F | 100(10) | 1/250 |
| 10 | % cells with C, 2+ | 2 | F | 100(10) | 1/250 |
| 11 | % cells with C, 3+ | 2 | F | 100(10) | 1/250 |
| 12 | % cells with M, 1+ | 2 | F | 100(10) | 1/250 |
| 13 | % cells with M, 2+ | 2 | F | 100(10) | 1/250 |
| 14 | % cells with M, 3+ | 2 | F | 100(10) | 1/250 |
| 15 | Epithelial cell size variation | 2 | F | 4 | 1/250 |
| 16 | lymphosite cell size variation | 2 | F | 4 | 1/250 |
| 17 | Stromal cell size variation | 2 | F | 4 | 1/250 |
| 18 | Mean of stained pixels | 1 | R | 100(10) | 1/1000 |
| 19 | Ratio of mean/std stained pixels | 1 | R | 100(10) | 1/1000 |
| 20 | Mean of CS pixels | 1 | R | 100(10) | 1/1000 |
| 21 | Ratio of CSmean/CSstd | 1 | R | 100(10) | 1/1000 |
| 22 | Magnification | I | F | 5 | 5/10/20/40/100 |
| 23 | Tissue type | I | F | * | |
| 24 | IHC marker | I | F | ** | |

Level: 1-4, 4- most significant and 1- least significant,
I-input information.
Nature: F—Fixed, R—Range
Possibilities: number of possibilities,
Weights: weight given to a parameter in computing similarity measure. Sum of weights is equal to "1".
$: These 101 levels are mapped into 10 zones.
* Tissue types: Breast, prostate, colon, bone marrow, liver, brain,
** Markers: ER, PR, P53, Ki67, Her2neu, P21, P27, DNA ploidy, AR, BCL-1, BCL-2, EGFR, TS, TOPO2, P16, P63, CD31, Cam5.2, . . .

Indexing Images with content descriptors using a similarity index: A simple method for storing and indexing images using a content descriptor is to use each of parametric values arriving at a key or index value. This method assumes that the computation of parametric values is consistent. However, in the case of life science research studies, many of the parametric values are given a range rather than a single value. As a result, searching for similar image based on exact match of content descriptors might give us a long list of indexes, often running into tens of thousands of images. Therefore there is a need to rank images in the order of "similarity", where similarity is from anatomic structures of interest point of view, which could be different from image point of view.

In one embodiment, a three part indexing method is used. A first part, includes parameter values that are fixed like magnification, tissue type are used to create separate set of image groups. A search based on text given in these fields is used. A second part, includes content based indexing uses organ-related description, specialized cells-related support-ing framework-related description, and foreign material-related description at field of view or tissue image level. The second part of index is used to create an image group 56 code. The third part includes parameters measured at individual objects level as well as pixel level image information. The third part is used to measure similarity between the input image and the images stored in the data base. Methods 34 and 44 illustrate this three part indexing method.

Figure 6:
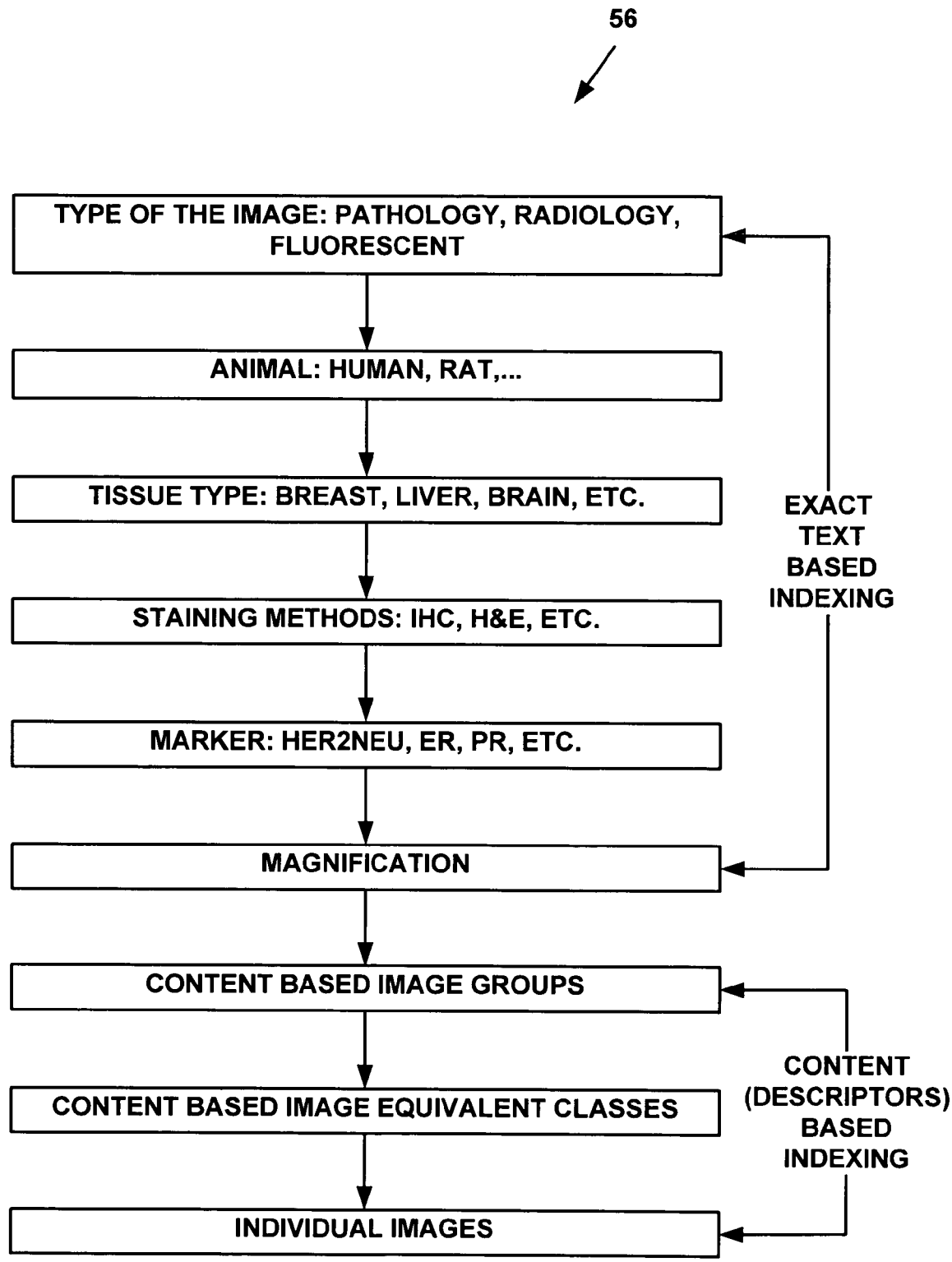
FIG. 6 is a flow diagram illustrating an exemplary method for image indexing.

FIG. 6 is a flow diagram illustrating an exemplary Method 56 for image indexing using content descriptors. However, the present invention is not limited to such an embodiment and other embodiments can also be used to practice the invention.

Figure 7:
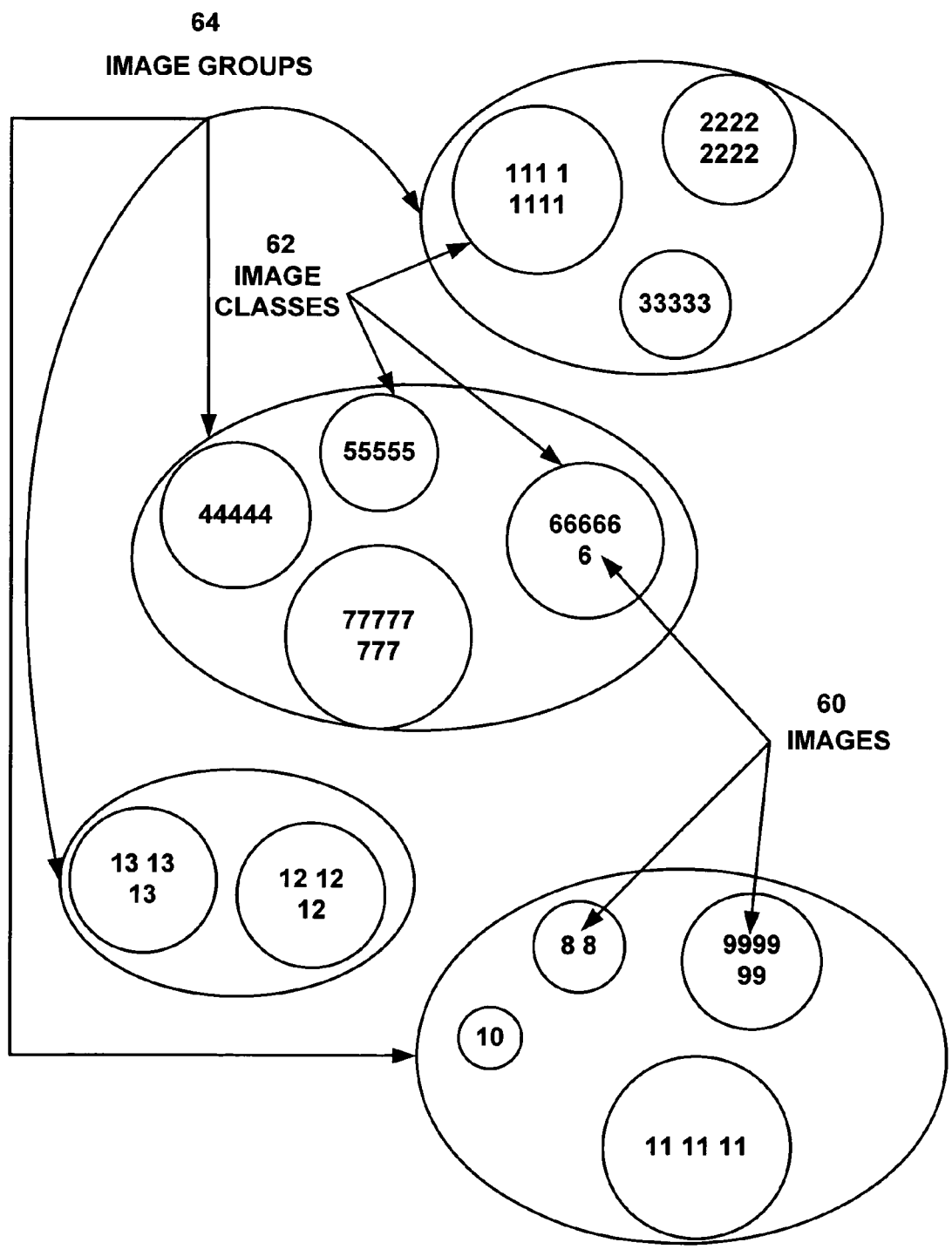
FIG. 7 is a data flow diagram illustrating an exemplary image hierarchy.

FIG. 7 is a data flow diagram 58 illustrating an exemplary digital image hierarchy 60. The image hierarchy includes plural digital images 62, plural image classes 64 and image groups 66. However, the present invention is not limited to such an embodiment and other embodiments can also be used to practice the invention.

In one embodiment, efficient indexing of images based on content description is achieved by image equivalent class 64 and image group 66 concepts. Digital images are categorized into equivalent classes 64. Two images are considered as belonging to the same class 64 if defined pathological/radiological descriptors match. Term descriptor matching is used instead of identical values to provide variations in measurement from person to person, variation due to illumination, and variation due to measuring equipment.

For example, an exemplary specimen might be given 55% C positivity by a pathologist, the same specimen another pathologist might give 53% C positivity. Therefore, there is a need to define zones, for percentages. In one embodiment, ten zones are used for classes 54. These ten zones are 0-9, 10-19, 20-29, 30-39, 40-49, 50-59, 60-69, 70-79, 80-89, 90-100 percent. However, the present invention is not limited to such an embodiment and other embodiments can also be used to practice the invention.

Figure 8:
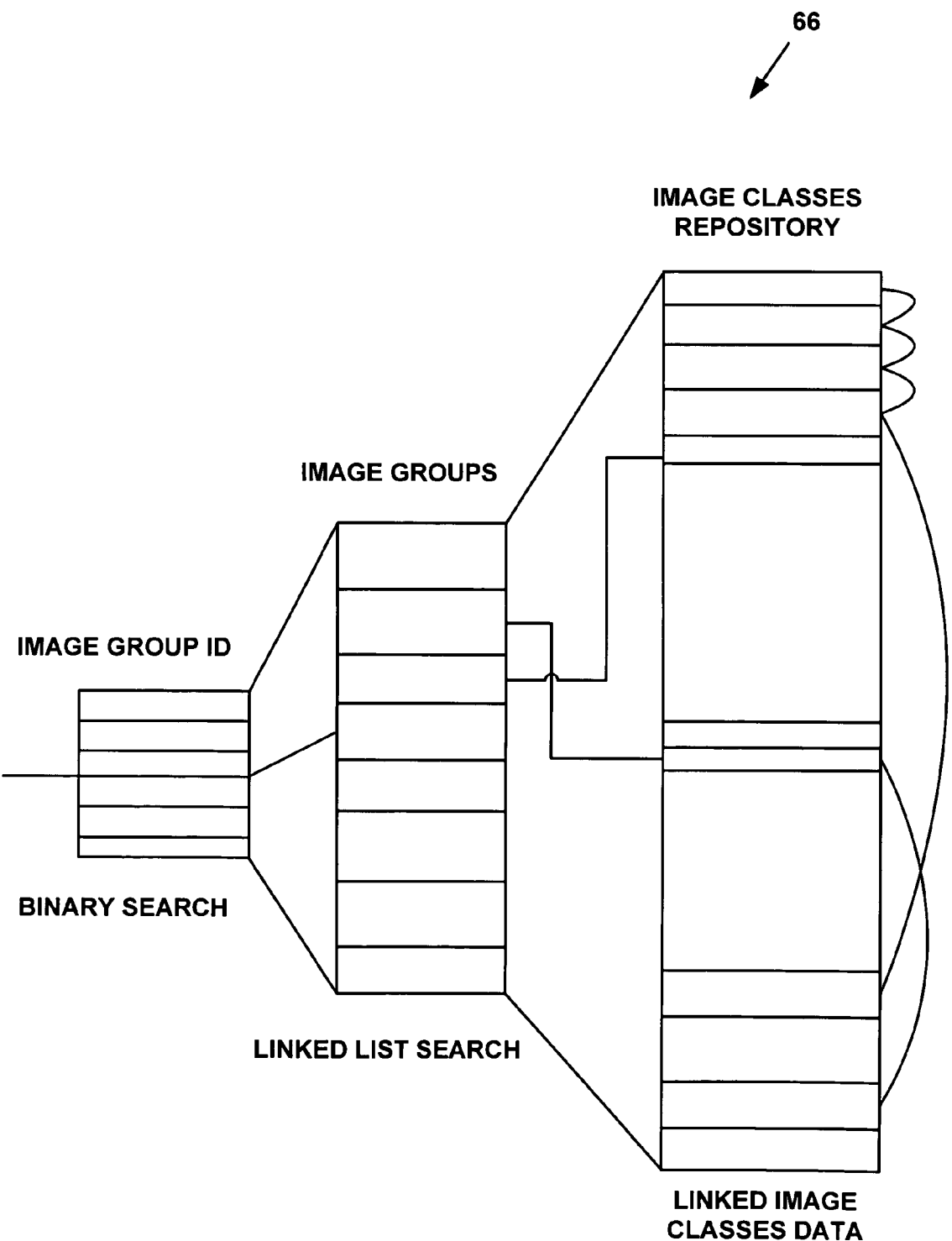
FIG. 8 is a flow diagram illustrating a method for content and image data storage architecture.

FIG. 8 is a flow diagram illustrating an exemplary content and image data storage architecture 66 based on the hierarchy of FIG. 7. However, the present invention is not limited to such an embodiment and other embodiments can also be used to practice the invention.

FIG. 9 illustrates block diagrams 68 of digital photographs 70, 72, 74, 76 which belong to three different image groups 66 based on membrane (Her2neu) scores.

FIG. 9 illustrates four images. These four images belong to three different image groups based on membrane (e.g., Her2neu, etc,) scores, where photographs A 70 and B 72 are from group one, photograph C 74 from group two and photograph D 76 from group three.

FIG. 10 illustrates block diagrams 78 of digital photographs 80, 82 illustrating a grouping 66 of images digital images based on membrane (e.g. Her2neu, etc.) scores.

FIG. 10 illustrates two fields of view of same specimen, both are Membrane (Her2neu) score 2+, but belong to two different image groups. Photograph A 80 includes a 99% positivity (in 90-100% range) and photograph B 82 includes a 71% positivity (in 70-79% range).

FIG. 11 is a block diagram illustrating an exemplar image group 66 identifier composition 84.

FIG. 11 illustrates a method for composing an image group 66 code (Imagegroupcode) 86 for IHC staining Percentage positivity is mapped from 0-100% to ten zones, namely 0-9, 10-19, 20-29, 30-39, 40-49, 50-59, 60-69, 70-79, 80-89, 90-10. Mapping of percentage positivity into zones is done to reduce the sensitivity of measurement. However, the present invention is not limited to such an embodiment and other embodiments for IHC staining and other embodiment for other types of stain can also be used.

Images belonging to an image group 66 are divided into image equivalent classes 64 depending on the values of individual parameters. Two images are said to be "equivalent" from anatomic structure point of view if every anatomic structure descriptor has values in the same range. Here again, a sensitivity factor is considered. Some of the parameters might vary by few percent if a part of the image is considered instead of the total image. Parameters are analyzed and mapped such that the variation between values for an image are classified into an equivalent class 64.

Similarity measure: It is likely that in most of the times one or more parameter values in the content description vary for the same specimen captured using two different devices or using same device at two different times. In one embodiment a similarity measure between a pair of images is used to determine the proximity of a given image to images from an image class 64 is used.

Similarity "$S_j$" between two images query image "Q" and a reference image "$R_j$ (representing jth class in the group), is defined in Equation (1)

$$S_j = 1 - \text{SQRT}(D_{jk})$$

$$D_{jk} = \text{SUM}(\text{SQUARE}(((P_q - P_{r_j})/\max(P_q, P_{r_j}))*wk)), \text{ for } k=1 \text{ to } M, \quad (1)$$

where "wk" is the weight given for k'th parameter in the table and M is the total number of parameters. However, the present invention is not limited to such an embodiment and other similarity embodiments can also be used to practice the invention.

In the identified image group 66, the image classes 64 are ranked based on the similarity $S_j$. The class with maximum $S_j$ is expected to be most similar to the query image. The image class 64 with least "$S_j$" is expected to be most dis-similar image class 64.

Storing Indexed Images

Storing: Available images, remote link to images available at other sources, meta data of the images, anatomical structures of interest parameters and respective image group 66 codes are stored in the system 10.

In one embodiment, image group 66 codes, and anatomical structures of interest parameters are stored in the primary memory. Actual images and links to other sources is stored in the secondary memory, on line. Meta data including image source, and other information is stored in the data base 18.

Figure 12:
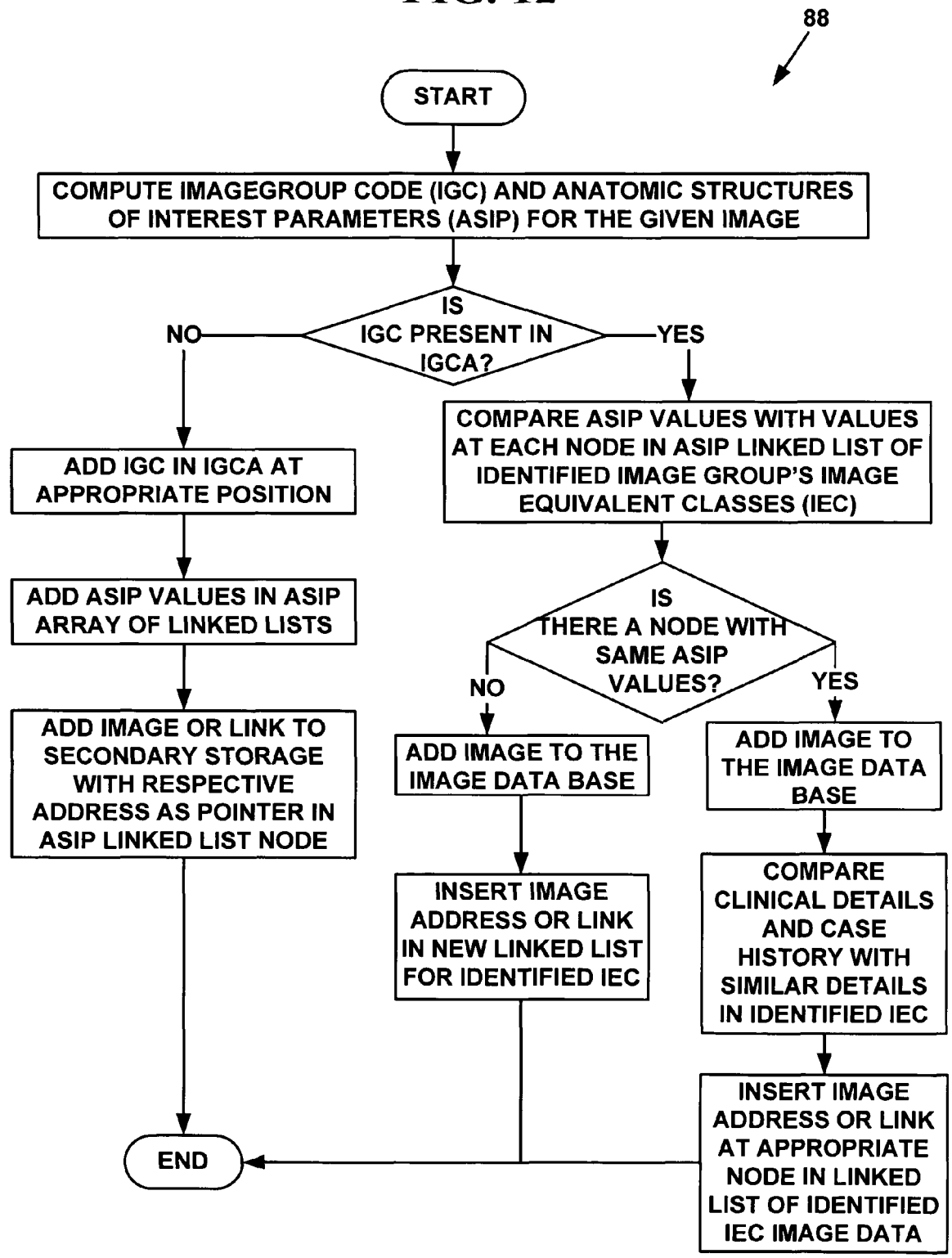
FIG. 12 is a flow diagram illustrating an exemplary method for storing image and anatomical structures of interest parameters.

FIG. 12 is a flow diagram illustrating an exemplary Method 88 for storing image and anatomical structures of interest parameters. However, the present invention is not limited to such an embodiment and other embodiments can also be used to practice the invention.

For each of these input images is computed in the manner illustrated in FIG. 9. Imagegroupcode table is searched to find out if the current image belongs to any of the existing Imagegroups using well known binary search method. If there is an existing group 66, other anatomical structures of interest parameters of the current image are compared with each of the image equivalent class parameters in the respective linked list. If there is a matching image equivalent class in the linked list, current image is added to the same in the secondary memory. Position of the current image in the image equivalent class is decided upon the clinical data and case history of the current image.

If there is no Imagegroup with the same code, new Imagegroupcode is inserted into the array of Imagegroupcodes. Inserting new Imagegroupcode at appropriate position is done using standard techniques.

Searching Indexed Images

Digital images are searched in two different ways. (1) using the method and system described herein to compute a same set of anatomic structures of interest descriptive parameters. A user can opt to modify these parameters. (2) Using a pre defined form with the methods and system described herein. This form includes same fields as computed by the software tool. Some of the fields will be mandatory in nature and others optional. A default value could be assumed for fields left blank. If the mandatory field is left blank, then default value corresponding to significant findings is assumed.

For example, in the case of IHC, user gives only membrane score as 3+, cytoplasm score negative and leaves two other mandatory fields blank. Then, default values of 100% nuclear percent positivity (e.g., digit value 9 in imagegroup code), 0% for cytoplasm percent positivity are assumed. Rational behind this assumption is, with cytoplasm negative, cytoplasm percentage positivity will be zero, images with 100% nuclear percent positivity are more significant than images with 50% nuclear percent positivity.

Image Group Code Search: Imagegroupcode is derived based on a database 18 query. If there is a matching entry in the Imagegroupcode array, corresponding group will be processed for identifying similar imageclass. If there is no matching entry in the Imagegroupcode array, the value compared last in the binary search will be used as the nearest group. Imagegroupcode array is sorted in decreasing order. Comparison is done using binary search, hence the last value in the array is the nearest value.

Parameters stored in the imageclasses linked lists are used for computing similarity measure for all imageclasses within the identified image group.

In the identified image group, the image classes are ranked based on the similarity $S_j$. The class with maximum $S_j$ is expected to be most similar to the query image. The class with least "$S_j$" is expected to be most dissimilar image class.

Figure 13:
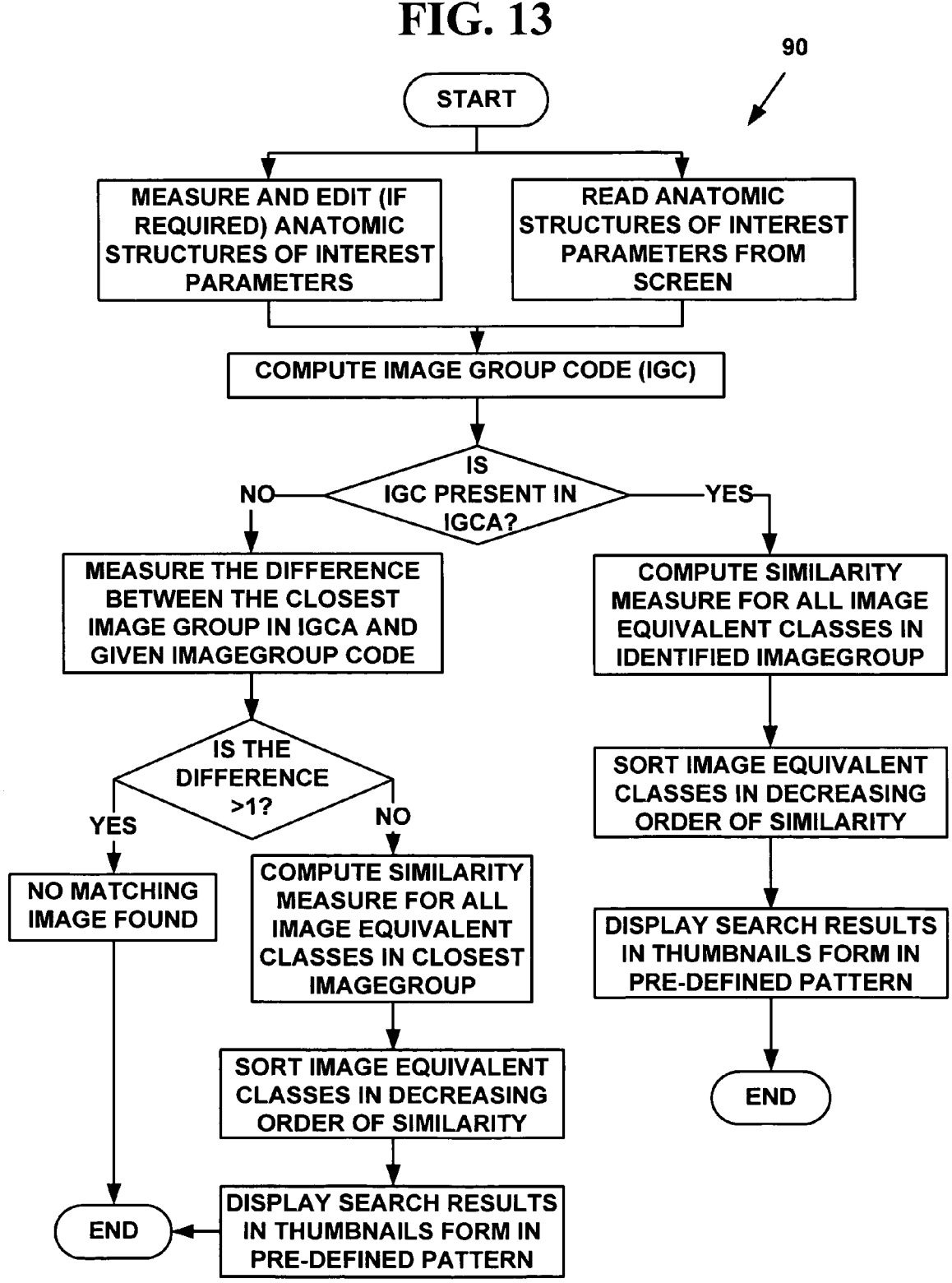
FIG. 13 is a flow diagram illustrating an exemplary searching method.

FIG. 13 is a flow diagram illustrating an exemplary searching Method 90 for indexed images. However, the present invention is not limited to such an embodiment and other embodiments can also be used to practice the invention.

FIG. 13 illustrates a Method 88 for searching similar indexed images from image databases 18 based on anatomical structures of interest parameters. These anatomic structures of interest parameters could be either measured through a software tool automatic or given through an interactive computer screen or through a form. Imagegroupcode for the given input image are computed using these parameters following the method illustrated in FIG. 9.

Presence of a matching image group code in the existing Imagegroupcode array is determined by searching the Imagegroupcode array using binary search method.

If an identical imagegroupcode is found in Imagegroupcode array, then the corresponding image group is processed to measure similarity between the query image and each of the image equivalent class in the identified image group. Image equivalent classes in the image group are sorted in decreasing order of similarity. Similarity is measured using the Equation (1). Sorted image equivalent classes forms the basis for presenting search results in an order. A Quicksort method is used to sort the similarity measurements. However, other methods can also be used.

If an identical image group code is not found, then the last value compared in binary search gives nearest Imagegroupcode. Difference between the given input imagegroupcode and the nearest imagegroupcode in the Imagegroupcode array is computed by summing the absolute value of difference between each of the four parameters used for deriving Imagegroupcode. That is, the difference between a query imagegroupcode "Q" and reference imagegroupcode "R" is illustrated in Equation (2).

$$\text{Difference} = ABS(Q_{pp} - R_{pp}) + ABS(Q_{cp} - R_{cp}) + ABS(Q_{ms} - R_{ms}) + ABS(Q_{cs} - R_{cs}) \qquad (2)$$

where $Q_{pp}, R_{pp}$, represents percentage positivity of query image, reference image respectively. $Q_{cp}, R_{cp}$ represents cytoplasm positivity of query image, reference image respectively, $Q_{ms}, R_{ms}$ represents membrane score of query image, reference image respectively and $Q_{cs}, R_{cs}$, represents cytoplasm score of query image, reference image respectively.

If the "Difference" is more than "1", then it is concluded that there is no similar image in the image data base. If the "Difference" is "1", then it could be due to variation in measurement, image equivalent classes in image group with difference value of "1" are measured for similarity and sorted on similarity measure. Sorted image equivalent classes are displayed in pre-defined pattern Search Results: Search results are displayed as a two dimensional array of thumbnails. First row corresponds to the thumbnails of image class most similar, with a navigational facility to browse other images in the same class.

Each row corresponds to an image equivalent class, in the order.

Figure 14:
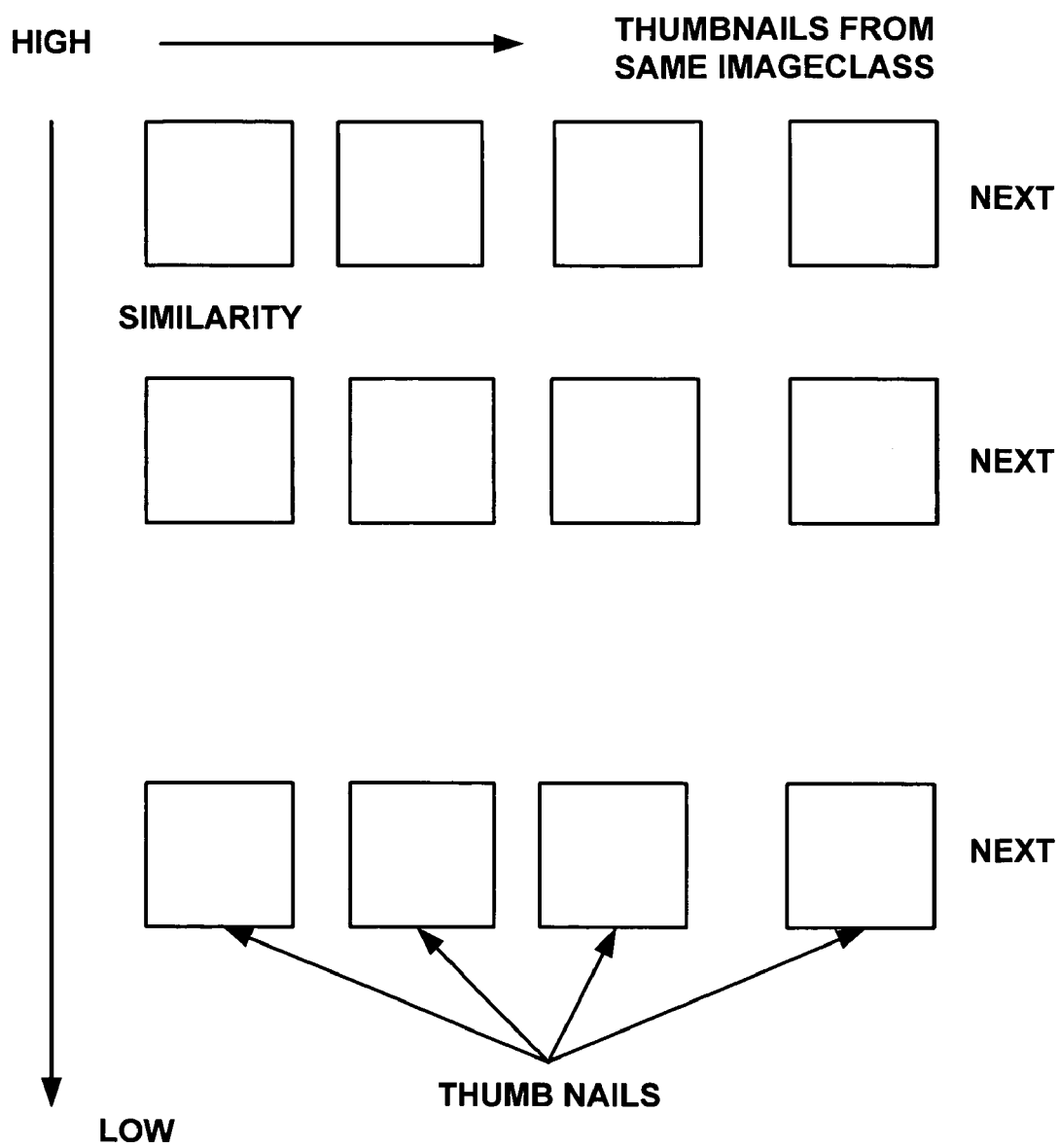
FIG. 14 is a block diagram illustrating exemplary search results display.

FIG. 14 illustrates an exemplary pre-defined pattern 92 for displaying thumbnail images. However, the present invention is not limited to such an embodiment and other embodiments can also be used to practice the invention.

APPLICATIONS: The method and system described here can be practiced in several different applications in life science research and industry. However, the present invention is not limited to the applications described and the inventions Histopathology: Prostate: The prostate gland contains three major glandular regions—the peripheral zone, the central zone, and the transition zone—which differ histologically and biologically. The central zone is relatively resistant to carcinoma and other disease; the transition zone is the main site of origin of prostate hyperplasia. There are also several important nonglandular regions concentrated in the anteromedial portion of the gland. Each glandular zone has specific architectural and stromal features. In all zones, both ducts and acini are lined by secretory epithelium. In each zone, there is a layer of basal cells beneath the secretory lining, as well as interspersed endocrine-paracrine cells. Frequent deviations from normal histology include post-inflammatory atrophy, basal cell hyperplasia, benign nodular hyperplasia, atypical adenomatous hyperplasia, and duct-acinar dysplasia.

Breast H&E: Breast TNM: Cells that are to be analyzed by the S-B-R system for tumor malignancy are examined for three types of structures: (1) mitotic structures; (2) anaplasia, or nuclear pleomorphism; and (3) ductoglandular differentiation. The presence and/or absence of these structures determines the degree of differentiation exhibited by the tumor cell. A well differentiated cell (e.g., normal breast tissue cell) is considered non-malignant and given a low S-B-R score. An undifferentiated cell or a cell which contains indices of frequent mitosis is considered malignant and given a high S-B-R score. Table 2 illustrates exemplary Breast H&E parameters.

TABLE 2

| Sl. no | Parameter | Level | Nature | possibilities | weights |
|---|---|---|---|---|---|
| 1 | Tubule score | 4 | F | 3 | 1/5 |
| 2 | N score (Pleomorphism) | 4 | F | 3 | 1/5 |
| 3 | Mitosis | 4 | F | 3 | 1/5 |
| 4 | Overall grade | 4 | F | 3 | 1/5 |
| 5 | % anaphase mitotic cells | 3 | F | | 1/45 |
| 6 | % telophase mitotic cells | 3 | F | | 1/45 |
| 7 | % prophase mitotic cells | 3 | F | | 1/45 |
| 8 | % metaphase mitotic cells | 3 | F | | 1/45 |
| 9 | tubular formation | 3 | F | 3 | 1/45 |
| 10 | Lining cell formation | 3 | F | | 1/45 |
| 11 | Glandular formation | 3 | F | | 1/45 |
| 12 | Capillary formation | 3 | F | | 1/45 |
| 13 | % cells with uniform chromatin pattern | 2 | F | 10 | 1/315 |
| 14 | % cells with coarse chromatin pattern | 2 | F | 10 | 1/315 |
| 15 | % cells with crumped chromatin pattern | 2 | F | | 1/315 |
| 16 | Nuclei size variation | 2 | F | | 1/315 |
| 17 | Nuclei shape variation | 2 | F | | 1/315 |
| 18 | % of cells with vesicular nuclei | 2 | F | | 1/315 |
| 19 | Mean of stained pixels | 1 | R | 100(10) | 1/1260 |
| 20 | Ratio of mean/std stained pixels | 1 | R | 100(10) | 1/1260 |
| 21 | Mean of CS pixels | 1 | R | 100(10) | 1/1260 |
| 22 | Ratio of CSmean/CSstd | 1 | R | 100(10) | 1/1260 |
| 23 | Magnification | I | F | | |
| 24 | Tissue type | I | F | | |
| 25 | Staining | I | F | | |

In Fluorescence in Situ Hybridization (FISH)

In Fluorescence in Situ Hybridization (FISH) a fluorescently labeled oligonucleotide probe is added to a tissue sample on a microscope slide under conditions that allow for the probe to enter the cell and enter the nucleus. If the labeled sequence is complementary to a sequence in a cell on the slide a fluorescent spot will be seen in the nucleus when the cell is visualized on a fluorescent microscope. Table 3 illustrates FISH parameters.

TABLE 3

| Sl. no | Parameter | Level | Nature | possibilities | weights |
|---|---|---|---|---|---|
| 1 | Amplification level | 4 | F | 3 | 1/2 |
| 2 | Amplification | 3 | F | 10 | 1/6 |
| 3 | Total number of interphase nuclei | 3 | F | 4 | 1/6 |
| 4 | Max orange/green | 2 | F | 4 | 1/24 |
| 4 | % interphase nuclei with o/g < 1 | 2 | F | 4 | 1/24 |
| 5 | % interphase nuclei with o/g = 1 | 2 | F | 4 | 1/24 |
| 6 | % interphase nuclei with o/g > 1 | 2 | F | 4 | 1/24 |
| 7 | Tissue type | I | F | | |
| 8 | Stain | I | F | 2 | | where o/g is a number of orange signals/number of green signals.

Table 4 illustrates Cytology and Flowcytometry.

TABLE 4

| Sl. no | Parameter | Level | Nature | possibilities | weights |
|---|---|---|---|---|---|
| 1 | Total number of cells | 4 | R | 10 | 1/2 |
| 2 | Intensity | 3 | F | 10 | 1/6 |
| 3 | Std Dev of intensity. | 3 | F | 3 | 1/6 |
| 4 | mean outgrowth per cell | 2 | F | 10 | 1/36 |
| 5 | total outgrowth | 2 | F | 10 | 1/36 |
| 6 | mean number of processes per cell over | 2 | F | 10 | 1/36 |
| 7 | total number of processes | 2 | F | 10 | 1/36 |
| 8 | Mean cell body | 2 | F | 10 | 1/36 |
| 9 | Total cell body | 2 | F | 10 | 1/36 |
| 10 | Tissue type | I | | | |
| 11 | Stain | I | | | |
| 12 | Organism, if any | I | | | |

Table 5 illustrates Cytopathology.

TABLE 5

| Sl. no | Parameter | Level | Nature | possibilities | weights |
|---|---|---|---|---|---|
| 1 | Unremarkable cells | 4 | F | 4 | 1/4 |
| 2 | Cellularity | 4 | F | 4 | 1/4 |
| 3 | Background | 4 | F | 10 | 1/4 |
| 4 | % of cells showing atypical High-grade nuclear changes | 3 | F | 10 | 1/24 |
| 5 | % of cells showing atypical Low-grade nuclear changes | 3 | F | 10 | 1/24 |
| 6 | % of cells showing atypical nuclear changes. inclusions | 3 | F | 10 | 1/24 |
| 7 | Inflammatory cell component: | 3 | F | 3 | 1/24 |
| 8 | chronic cell component: | 3 | F | 4 | 1/24 |
| 9 | Intensity | 2 | F | 10 | 1/48 |
| 10 | Std Dev of intensity. | 2 | F | 3 | 1/48 |
| 11 | Tissue type | I | | | |
| 12 | Stain | I | | | |
| 13 | Organism, if any | I | | | |

Table 6 illustrates 2D Gels.

TABLE 6

| Sl. no | Parameter | Level | Nature | possibilities | weights |
|---|---|---|---|---|---|
| 1 | Ppm intensity | 4 | F | | 1/3 |
| 2 | Spot quality variation | 4 | F | | 1/3 |
| 3 | Spot size variation | 3 | F | | 1/15 |
| 4 | Spot shape variation | 3 | F | | 1/15 |
| 5 | Average number of spots per column/total number of spots | 3 | F | | 1/15 |
| 6 | Average number of spots per row/total number of spots | 3 | F | | 1/15 |
| 7 | Spot intensity variation | 2 | | | 1/45 |
| 8 | Total number of spots | 2 | F | | 1/45 |
| 9 | Total area of spots | 2 | F | | 1/45 |
| 10 | Gel type | I | F | | |
| 11 | Stain | I | F | 3 | |

Radiology: Over the last decade or so, many investigators have carried out basic studies and clinical applications toward the development of modern computerized schemes for detection and characterization of lesions in radiologic images. Advances have been made in the computerized analysis of digital chest images, especially the detection of pulmonary nodules, using such techniques as artificial neural networks, temporal subtraction, and dual-energy imaging. Various observer performance studies have documented the benefit of radiologists using a computer aid in their interpretation process. Similar strides have been made with breast imaging with the aims of increased patient management. CAD research in breast imaging is now including digital mammography, ultrasound, and magnetic resonance imaging. The method and system can be used for automated radiology analysis.

Chest Imaging. Some of the key parameters measured in chest images are—pulmonary nodules, interstitial infiltration, abnormal asymmetry, texture, bronchial branches, lobar shape and surface-shape. The method and system can be used for automated chest image analysis.

Breast Imaging. Some of the key parameters measured in breast images are missed lesions, clustered microcalcifications, mass, texture and shape. The method and system can be used for automated breast image analysis.

Vascular Imaging. Some of the key parameters measured in vascular images cranial vessels malformations, cerebral arteriovenous malformations, vascular stenosis, atherosclerotic plaques morphology, size of the lesion. The method and system can be used for automated vascular image analysis.

Several image classes are grouped together into an Image-group. The basis for grouping image classes into an Image-group is that these classes have same overall interpretation, but might differ in the details. For example, two specimens might have identical "C" score and "M" score, but have different percentage of cells with membrane 2+.

Images within an image equivalent class are ordered based on the available non-image information like significant findings in clinical data and case history. That is, the images corresponding to case with significant findings in clinical data or past history are given higher priority and displayed first.

The method and system described herein is also used to create additional knowledge. The additional knowledge is created using the method and system described herein.

Figure 15:
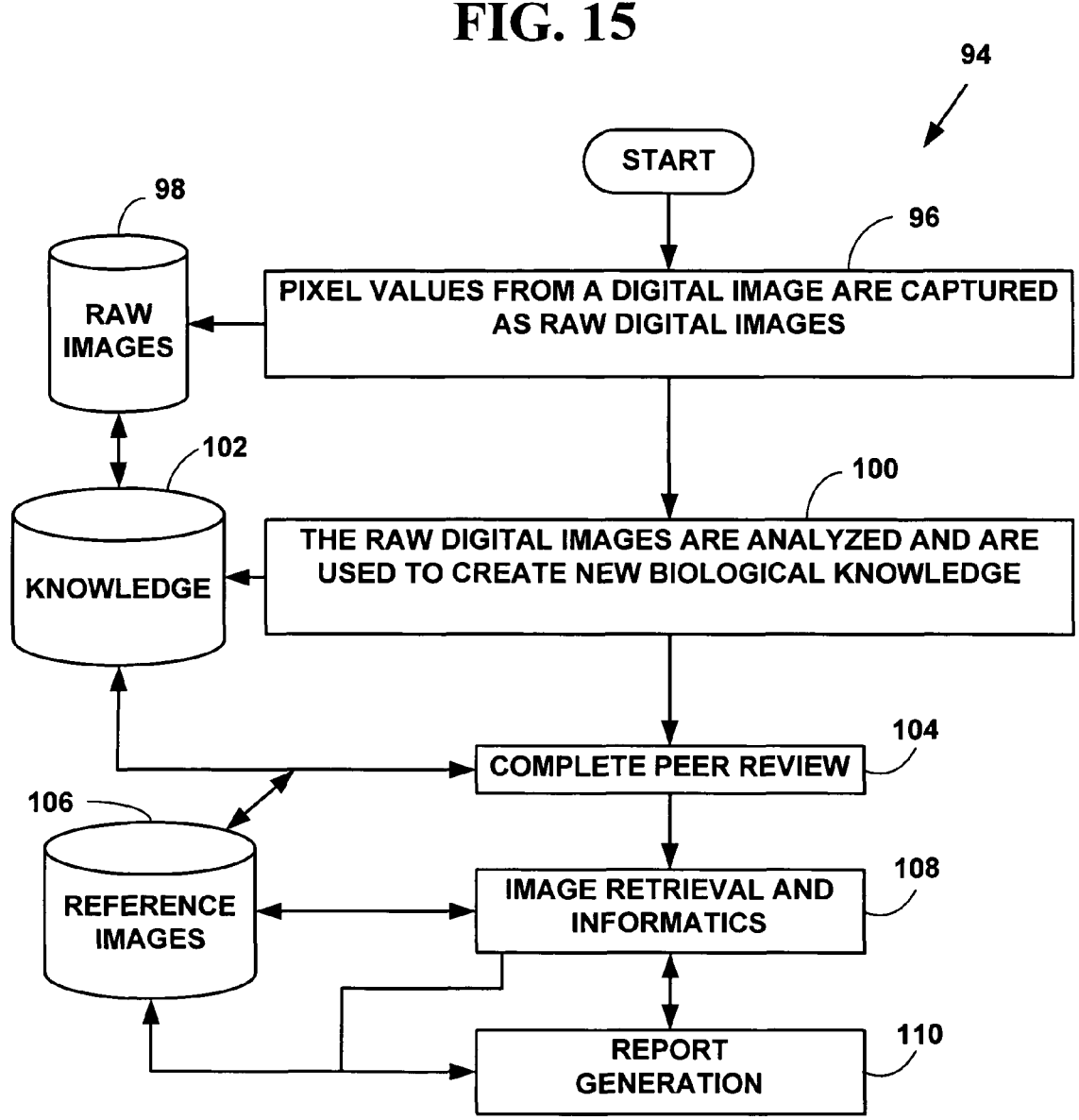
FIG. 15 is a block diagram illustrating an exemplary flow of data in the automated analysis system.

FIG. 15 is a block diagram illustrating an exemplary flow of data 94 in the automated analysis system 10. Pixel values from a digital image of a biological sample to which a chemical compound has been applied are captured 96 as raw digital images 98. The raw digital images 98 are stored in raw image format in one or more image databases 22. Parameters from individual biological components within the biological sample are analyzed on the digital image and are used to create new biological knowledge 100 using the methods described herein. The new biological and medical knowledge is stored in a knowledge database 102. Peer review of the digital image analysis and medical, life science and biotechnology experiment results is completed 104. A reference digital image database 106 facilitates access of reference images from previous records of life science and biotechnology experiments at the time of peer review. Contents of the reference digital image database 106, information on the biological sample and analysis of current biological sample are available at an image retrieval, reporting and informatics module 108 that displays information on GUI 14. Conclusions of a medical diagnosis or prognosis or life science and biotechnology experiment are documented as one or more reports. Report generation 10 allows configurable fields and layout of the report. New medical, biological and/or biotechnology knowledge is automatically created and saved.

In one embodiment of the invention, the methods and systems described herein are completed within an Artificial Neural Networks (ANN). An ANN concept is well known in the prior art. Several text books including "Digital Image Processing" by Gonzalez R C, and Woods R E, Pearson Education, pages 712-732, 2003 deals with the application of ANN for classification of patterns.

In one embodiment, an ANN based on FIG. 15 is used for training and classifying tissue samples from automated analysis over a pre-determined period of time. However, the present invention is not limited to such an embodiment and other embodiments can also be used to practice the invention. The invention can be practiced without used of an ANN The present invention is implemented in software. The invention may be also be implemented in firmware, hardware, or a combination thereof, including software. However, there is no special hardware or software required to use the proposed invention.

It should be understood that the architecture, programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

While various elements of the preferred embodiments have been described as being implemented in software, in other embodiments hardware or firmware implementations may alternatively be used, and vice-versa.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

We claim:

1. An automated method for indexing a plurality of anatomical structures of interest in a plurality of digital images, comprising: determining organ level details of a plurality of anatomical structures of interest in a plurality of digital images of one or more biological tissue samples to which a chemical compound has been applied; determining cell level details of the plurality of anatomical structures of interest in the plurality of digital images; determining foreign material level details of the plurality of anatomical structures of interest in the plurality of digital images; and indexing the plurality of digital images using the plurality of determined details with a predetermined indexing scheme, thereby allowing a medical conclusion to be determined from the indexed plurality of digital images.

2. The method of claim 1 further comprising a computer readable medium having stored therein instructions for causing one or more processors to execute the steps of the method.

3. The method of claim 1 further comprising determining framework level details of the plurality of anatomical structures of interest in the plurality of digital images.

4. The method of claim 1 wherein the biological sample is a human tissue sample.

5. The method of claim 1 wherein the pre-determined indexing scheme includes an information hierarchy using big files, repositories, document indexes, lexicons and inverted indexes for classifying the plurality of details determined for plurality of anatomical structures in the plurality of digital images.

6. The method of claim 1 wherein the medical conclusion is a human cancer diagnosis.

7. The method of claim 6 wherein the human cancer diagnosis includes a human breast cancer or a human prostrate cancer diagnosis.

8. The method of claim 1 wherein the pre-determined indexing scheme includes using a plurality of content descriptors with parametric values determining a key or index value for the plurality of digital images.

9. The method of claim 1 wherein the wherein the pre-determined indexing scheme includes an information hierarchy with a plurality of digital images at a lowest level, a plurality of digital image classes a next level and a plurality of digital image groups at a highest level.

10. An automated method for indexing a plurality of anatomical structures of interest in a plurality of digital images, comprising: determining pixel level details of a plurality of anatomical structures of interest in a plurality of digital images of one or more biological samples to which a chemical compound has been applied; determining object level details of the plurality of anatomical structures of interest in the plurality of digital images; determining semantic or context based level details of the plurality of anatomical structures of interest in the plurality of digital images; and indexing the plurality of digital images using the plurality of determined details with a pre-determined indexing scheme, thereby allowing a medical conclusion from the indexed plurality of digital images.

11. The method of claim 10 further comprising a computer readable medium having stored therein instructions for causing one or more processors to execute the steps of the method.

12. The method of claim 10 further comprising determining knowledge based level details of the plurality of anatomical structures of interest in the plurality of digital images.

13. The method of claim 10 wherein the biological sample is a human tissue sample.

14. The method of claim 10 wherein the predetermined indexing scheme includes an information hierarchy using big files, repositories, document indexes, lexicons and inverted indexes for classifying the plurality of details determined for plurality of anatomical structures in the plurality of digital images.

15. The method of claim 10 wherein the medical conclusion is a human cancer diagnosis.

16. The method of claim 15 wherein the human cancer diagnosis includes a human breast cancer or a human prostrate cancer diagnosis.

17. The method of claim 10 wherein the pre-determined indexing scheme includes using a plurality of content descriptors with parametric values determining a key or index value for the plurality of digital images.

18. The method of claim 10 wherein the wherein the pre-determined indexing scheme includes an information hierarchy with a plurality of digital images at a lowest level, a plurality of digital image classes a next level and a plurality of digital image groups at a highest level.

19. The method of claim 10 wherein the indexing step comprises: determining a plurality of fixed parameters including magnification and tissue type, thereby creating a set of digital images of interest; determining a plurality of organ-related descriptions, specialized cells-related supporting framework-related descriptions, and foreign material-related descriptions at a field of view or tissue image level, thereby creating an image group code; and determining parameters measured at an individual object level and a pixel level, thereby measuring a similarity between an input digital image and a plurality of other digital images.

20. The method of claim 10 wherein the indexing step includes determining a similarity index using the using the plurality of determined details of the plurality of anatomical structures of interest.

21. The method of claim 10 wherein the indexing step includes indexing the plurality of digital images using remote links to the plurality of digital images stored at other sources, meta data for the plurality of digital images, anatomical structures of interest parameters and image group codes created for the digital images to store the plurality of digital images in an index hierarchy.

22. The method of claim 10 further comprising: searching the indexed plurality of digital images for similar digital images; and displaying the similar indexed digital images as a two-dimensional array of thumbnail digital images.

23. An automated system for indexing a plurality of anatomical structures of interest in a plurality of digital images, comprising in combination: means for determining organ details of a plurality of anatomical structures of interest in a plurality of digital images of one or more biological tissue samples, determining cell level details of the plurality of anatomical structures of interest in the plurality of digital images and determining foreign material level details of the plurality of anatomical structures of interest in the plurality of digital images; means for determining pixel level details of a plurality of anatomical structures of interest in a plurality of digital images of one or more biological samples, determining object level details of the plurality of anatomical structures of interest in the plurality of digital images and determining semantic or context based level details of the plurality of anatomical structures of interest in the plurality of digital images; means for indexing the plurality of digital images using the plurality of determined details with a pre-determined indexing scheme, thereby allowing a medical conclusion from the indexed plurality of digital images; means for searching the indexed plurality of digital images for similar digital images; and means for displaying the similar indexed digital images.

* * * * *